US010260054B2

(12) United States Patent
Pegan et al.

(10) Patent No.: US 10,260,054 B2
(45) Date of Patent: Apr. 16, 2019

(54) ENGINEERED ORGANOPHOSPHORUS ACID ANHYDROLASES AND METHODS OF USE THEREOF

(71) Applicants: University of Georgia Research Foundation, Inc., Athens, GA (US); The United States of America, as represented by the Secretary of the Army, Washington, DC (US)

(72) Inventors: Scott Pegan, Athens, GA (US); Steven P. Harvey, Lutherville, MD (US)

(73) Assignees: University of Georgia Research Foundation, Inc., Athens, GA (US); The United States of America, as represented by the Secretary of the Army, Washington, DC (US)

( * ) Notice: Subject to any disclaimer, the term of this patent is extended or adjusted under 35 U.S.C. 154(b) by 212 days.

(21) Appl. No.: 15/174,719

(22) Filed: Jun. 6, 2016

(65) Prior Publication Data
US 2016/0355792 A1 Dec. 8, 2016

Related U.S. Application Data

(60) Provisional application No. 62/171,727, filed on Jun. 5, 2015.

(51) Int. Cl.
*C12N 9/16* (2006.01)
*A61K 31/55* (2006.01)
*A61L 2/16* (2006.01)
*A61K 31/44* (2006.01)
*A61K 31/46* (2006.01)
*A61K 38/00* (2006.01)
*A61K 31/5513* (2006.01)
*A61K 31/4425* (2006.01)

(52) U.S. Cl.
CPC ............ *C12N 9/16* (2013.01); *A61K 31/4425* (2013.01); *A61K 31/46* (2013.01); *A61K 31/5513* (2013.01); *A61L 2/16* (2013.01); *C12Y 301/08002* (2013.01); *A61K 38/00* (2013.01)

(58) Field of Classification Search
None
See application file for complete search history.

(56) References Cited

U.S. PATENT DOCUMENTS

| | | |
|---|---|---|
| 5,928,927 A | 7/1999 | Cheng |
| 6,017,750 A | 1/2000 | Harvey et al. |
| 6,080,566 A | 6/2000 | Cheng |
| 6,541,230 B1 | 4/2003 | Gordon |
| 6,716,450 B1 | 4/2004 | Yin |
| 7,229,819 B1 | 6/2007 | Cheng et al. |
| 7,723,558 B1 | 5/2010 | Cheng |
| 9,017,982 B1 | 4/2015 | Shah et al. |
| 9,587,232 B1 | 3/2017 | Harvey et al. |
| 9,617,526 B1 | 4/2017 | Harvey et al. |
| 9,976,130 B1 | 5/2018 | Guelta et al. |

OTHER PUBLICATIONS

Adams, et al., "PHENIX: a comprehensive Python-based system for macromolecular structure solution", Acta Crystallogr D-Biol Crystallogr., 66:213-21 (2010).
Benschop, et al., "Isolation, anticholinesterase properties, and acute toxicity in mice of the four stereoisomers of the nerve agent soman", Toxicol Appl Pharmacol., 72:61-74 (1984).
Bigley, et al., "Enzymatic Neutralization of the Chemical Warfare Agent VX: Evolution of Phosphotriesterase for Phosphorothiolate Hydrolysis", J Am Chem Soc., 135:10426-32 (2013).
Buckley, et al., "Overcoming apathy in research on organophosphate poisoning", BMJ, 329:1231-3 (2004).
Cheng, et al., "Cloning and expression of a gene encoding a bacterial enzyme for decontamination of organophosphorus nerve agents and nucleotide sequence of the enzyme", ApplEnviron Microbiol., 62:1636-41 (1996).
Cheng, et al., "Nucleotide sequence of a gene encoding an organophosphorus nerve agent degrading enzyme from Alteromonas haloplanktis", J Ind Microbiol Biotechnol., 18:49-55 (1997).
Collaborative, "The CCP4 suite: programs for protein crystallography", Acta Crystallogr D-Biol Crystallogr., 50:760-3 (1994) Abstract Only.
Daczkowski, et al., Engineering the Organophosphorus Acid Anhydrolase Enzyme for Increased Catalytic Efficiency and Broadened Stereospecificity on Russian VX , Biochem., 54(41):6423-33 (2015).
Defrank, et al., "Purification and properties of an organophosphorus acid anhydrase from a halophilic bacterial isolate", J Bacteriol., 173:1938-43 (1991).
Defrank, et al., "Screening of halophilic bacteria and *Alteromonas* species for organophosphorus hydrolyzing enzyme activity", Chem Biol Interact., 87:141-8 (1993).
Emsley, et al., "Coot: model-building tools for molecular graphics", Acta Crystallog D-Biol Crystallogr.,60:2126-32 (2004).

(Continued)

*Primary Examiner* — Suzanne M Noakes
(74) *Attorney, Agent, or Firm* — Pabst Patent Group LLP

(57) ABSTRACT

Genetically engineered organophosphorus acid anhydrolases (OPAA) with improved catalytic efficiency and relaxed stereospecificity are provided. The variants typically include a mutation at the residue corresponding to H343 of wildtype *Alteromonas* sp. OPAA. The mutation allows the OPAA enzyme to effectively process both VR enantiomers. The OPAA opt

(56) References Cited

OTHER PUBLICATIONS

Genbank Accession No. AAB05590.1), "organophosphorus acid anhydrolase-2 [*Alteromonas* sp.]", 2 pages, first appeared Jul. 24, 1995, accessed Oct. 20, 2016.

Harvey, et al., "Stereospecificity in the enzymatic hydrolysis of cyclosarin (GF)", Enzyme Microbial Technol., 37:547-55 (2005).

Huang, et al., "Aminopeptidase p mediated detoxification of organophosphonate analogues of sarin: mechanistic and stereochemical study at the phosphorus atom of the substrate", Chembiochem., 7:506-14 (2006).

Mesecar, et al., "Orbital steering in the catalytic power of enzymes: small structural changes with large catalytic consequences", Science, 277:202-6 (1997).

Petrikovics, et al., "Long circulating liposomes encapsulating organophosphorus acid anhydrolase in diisopropylfluorophosphate antagonism", Toxicol Sci., 57:16-21 (2000).

Tsai, et al., "Enzymes for the homeland defense: optimizing phosphotriesterase for the hydrolysis of organophosphate nerve agents", Biochem, 51:6463-75 (2012).

Uniprot Accession No. Q44238, RecName: Full=Xaa-Pro dipeptidase; Short=X-Pro dipeptidase: AltName: Full=DFPase; AltName: Full=Imidodipeptidase; AltName: Full=Organophosphorus acid anhydrolase 2; Short=OPAA-2; AltName: Full=Paraoxon hydrolase; AltName: Full=Phosphotriesterase; AltName: Full . . . , 9 pages, first appeared Sep. 14, 2005, accessed Oct. 20, 2016.

Vyas, et al., "Structural insights into the dual activities of the nerve agent degrading organophosphate anhydrolase/prolidase.", Biochem., 49:547-59 (2010).

Yeung, et al., "A gas chromatographic-mass spectrometric approach to examining stereoselective interaction of human plasma proteins with soman", J Anal Toxicol., 32:86-91 (2008).

Hall, et al., "Differences between some biological properties of enantiomers of alkyl S-alkyl methylphosphonothioates," *J Pharm Pharmacol.*, 29(9):574-6 (1977).

Kacu, et al., "Russian VX: Inhibition and Reactivation of Acetylcholinesterase Compared with VX Agent," *Basic Clin Pharmacol Toxicol.*, 98(4):389-94 (2006).

ENGINEERED ORGANOPHOSPHORUS ACID ANHYDROLASES AND METHODS OF USE THEREOF

CROSS-REFERENCE TO RELATED APPLICATIONS

This application claims the benefit of and priority to U.S. Provisional Application No. 62/171,727, filed Jun. 5, 2015, which is specifically incorporated by reference herein in its entirety.

STATEMENT REGARDING FEDERALLY SPONSORED RESEARCH

This invention was made with government support made available by the Defense Threat Reduction Agency CB3742 (SPH). The government has certain rights in the invention.

REFERENCE TO THE SEQUENCE LISTING

The Sequence Listing submitted as a text file named "UGA_2330_ST25.txt," created on Jun. 6, 2016, and having a size of 47,401 bytes is hereby incorporated by reference pursuant to 37 C.F.R. § 1.52(e)(5).

FIELD OF THE INVENTION

This invention is generally directed to genetically engineered organophosphorus acid anhydrolase polypeptides with broadened stereospecificity and increased activity for acetylcholinesterase-inhibiting organophosphorus compounds, and methods of use thereof.

BACKGROUND OF THE INVENTION

The potential threat of an intentional release of chemical nerve agents along with thousands of fatalities in developing countries every year caused by pesticide poisoning has made treatments for these types of poisoning a persistent focus (Eddleston, *QJM: Monthly Journal of the Association of Physicians*, 93:715-731 (2000); Phillips, et al., *Lancet*, 359: 835-840 (2002)). Many pesticides and chemical nerve agents rely on the same organophosphate core to inhibit acetylcholinesterases. For example, G-type nerve agents such as soman (o-pinacolyl methylphosphonofluoridate) possess the same fluorophosphate moiety as the pesticide mipafox (N,N'-Diisopropyldiamidofluorophosphate; DD-FP). In the case of V-type nerve agents, the fluoride on the organophosphate core is substituted with a thiol group (Coulter, et al., *U.S. Army Chemical Warfare Laboratories Technical Report CWLR*, 2346 (1959)). Current treatments for organophosphate poisoning involve a combination of atropine (a muscarinic antagonist), pralidoxime (also known as 2-PAM, a reactivator of poisoned acetylcholinesterase enzymes) and benzodiazepines to control seizures (Buckley, et al., *BMJ*, 329:1231-1233 (2004)).

Another method of treating organophosphate poisoning has recently emerged through the potential use of catalytic enzymes to detoxify these poisons in the blood. Detoxification of these poisons offers the particular advantage of altering organophosphates before they enter the tissue where they bind acetylcholinesterase in the neuromuscular junctions. Therefore, such enzymes can at a minimum work in a complementary manner to, and in concert with, other treatments to improve survival rates. This co-treatment was demonstrated when a liposome-encapsulated diisopropylfluorophosphate (DFP)—hydrolyzing enzyme, known as an organophosphorus acid anhydrolase (OPAA) was used in conjunction with atropine and 2-PAM to confer 25 $LD_{50}$s of protection against diisopropylfluorophosphate (Petrikovics, et al., *Toxicological Sciences: An Official Journal of the Society of Toxicology*, 57:16-21 (2000)).

OPAA (EC 3.1.82) is one example of a larger class of enzymes known as phosphotriesterases, initially identified over sixty years ago and generally recognized for their ability to detoxify organophosphates (Bigley, et al., *Biochimica et Biophysica Acta*, 1834:443-453 (2013)). Phosphotriesterase (PTE), methyl parathion hydrolase (MPH), diisopropylfluorophosphatase (DFP) and paraoxonase 1 (PON1) are the other examples from this class (Bigley, et al., *Biochimica et Biophysica Acta*, 1834:443-453 (2013)). These enzymes are all hydrolases with hydrophobic active sites and a requirement for divalent metals but they differ in terms of sequence, structure and their catalytic mechanisms. The native activity of OPAA is that of a prolidase (Cheng, et al., *Journal of Industrial Microbiology & Biotechnology*, 18:49-55 (1997)). The OPAA enzyme from the gram-negative, aerobic, short rod bacterium *Alteromonas* sp. JD6.5 has drawn particular attention because it has very high activity on GD as well as a very high level of expression in *E. coli* (DeFrank, et al., *Chemico-Biological Interactions*, 87:141-148 (1993); DeFrank, et al., *Journal of Bacteriology*, 173: 1938-1943 (1991)). However, it has not been reported to have any activity against V-type nerve agents.

An effective broad-spectrum enzymatic antidote addressing nerve agent poisoning would need to include enzymes with good catalytic efficiency (target value of about $10^7$ $min^{-1} M^{-1}$) on as many relevant substrates as possible. Regrettably, the activity of the wild-type OPAA enzyme on VR (approximately $5\times10^2 M^{-1} min^{-1}$) falls well short of what is necessary for use in that capacity.

Furthermore, with enzyme-substrate interactions more often than not being very stereospecific, enhancing the catalytic activity of OPAA may only be one component necessary to achieve an effective catalytic antidote. Previous reports have already indicated that the toxicity of chemical nerve agents can be extremely stereospecific, as evidenced by the case of soman (o-pinacolyl methylphosphonofluoridate), where the most toxic C(−)P(−) enantiomer is more than 100 times as toxic as the least toxic C(+)P(+) enantiomer, corresponding to mouse $LD_{50}$ values of 38 µg/kg vs >5000 µg/kg, respectively (Benschop, et al., *Toxicology and Applied Pharmacology*, 72:61-74 (1984)). The differences in toxicity generally correspond to the different affinities with which the respective enantiomers bind acetylcholinesterase (Benschop, et al., *Toxicology and Applied Pharmacology*, 72:61-74 (1984)), although they may also be attributable to differential detoxification in vivo. For example, native enzymes such as human paraoxonase may preferentially catalyze the less toxic P(+) enantiomers of soman (Yeung, et al., *Journal of Analytical Toxicology*, 32:86-91 (2008)), thereby reducing the measure of their toxicity. Generally, it is known that the action of catalytic enzymes on nerve agents occurs in a stereospecific manner, both with G-agents (Harvey, et al., *Enzyme and Microbial Technology*, 37:547-555 (2005); Tsai, et al., *Biochemistry*, 51:6463-6475 (2012)) and with VX (Bigley, et al., *Journal of the American Chemical Society*, 135:10426-10432 (2013)). Although OPAA is easily produced at high levels and is stable in normal use, its activity against V-type chemical agents is extremely low and it shows an almost absolute preference for the less toxic enantiomers of soman.

Understandably, an effective enzymatic, broad-spectrum antidote to nerve agent poisoning would need to include enzymes that possess not only good catalytic efficiency on racemic materials, but activity specifically directed towards the toxic isomers of all relevant substrates. This combination of catalytic efficiency coupled with the proper stereochemistry was achieved recently with the H257Y/L303T mutant of the bacterial phosphotriesterase (PTE) enzyme for the substrates sarin, soman and cyclosarin (Tsai, et al., *Biochemistry*, 51:6463-6475 (2012)). The mutant enzyme possessed catalytic efficiencies approximately ten times greater than wild-type PTE on sarin and cyclosarin and approximately 100 times greater on soman, as well as a reversal of stereospecificity so that the mutant possessed greater activity on the more toxic P(-) isomer than the P(+)isomer (the wild-type enzyme prefers the P(+) isomer).

VX (O-ethyl S-[2-(diisopropylamino)ethyl] methylphosphonothioate), which is a structural isomer of VR, has about a 13-fold difference in toxicity between its enantiomers, with the P(-) isomer being the more toxic of the two (Hall, et al., *The Journal of Pharmacy and Pharmacology*, 29:574-576 (1977)). Given that VX and VR are structural isomers, have similar racemic toxicities (Benschop, et al., *Toxicology and Applied Pharmacology*, 72:61-74 (1984); Hall, et al., *The Journal of Pharmacy and Pharmacology*, 29:574-576 (1977)), and trends in cholinesterase inhibition constants with the respective enantiomers (the P(-) enantiomers of each are much more inhibitory); (Bigley, et al., *Journal of the American Chemical Society*, 135:10426-10432 (2013)), and that both are treated with similar modalities using acetylcholinesterase reactivators (Kuca, et al., *Basic & Clinical Pharmacology & Toxicology*, 98:389-394 (2006)), it is likely that the relative toxicity of their respective enantiomers follows a similar pattern. Therefore, there remains a need for improved OPAA enzymes.

It is an object of the invention to provide engineered OPAAs with increased catalytic efficiency for organophosphates, particular V-type nerve agents such as VX and VR.

It is a further object of the invention to provide engineered OPAAs with broadened stereospecificity capable of catalysis of both enantiomers of V-type nerve agents such as VX and VR.

It is also an object of the invention to provide methods of using engineered OPAAs to treat and inhibit nerve agent poisoning.

It is another object of the invention to provide methods of using engineered OPAAs in various detoxification applications.

SUMMARY OF THE INVENTION

Engineered organophosphorus acid anhydrolases (OPAA) with improved catalytic efficiency and relaxed stereospecificity are provided. The OPAAs typically include a mutation at the residue corresponding to H343 of wildtype *Alteromonas* sp. OPAA. The mutation allows the OPAA enzyme to effectively process both VR enantiomers. The OPAA optionally includes one or more mutations selected the residues corresponding to Y212, V342, and I215 of wildtype *Alteromonas* sp. OPAAs which can improve the enzyme's catalytic efficiency for VX and VR. A particularly preferred OPAA includes mutations at the residues corresponding Y212F, V342L, I215Y, and H343D relative to wildtype *Alteromonas* sp. OPAA. In particular embodiments, the OPAA has the amino acid sequence of SEQ ID NO:6, 7, 12, 14 or a catalytically active fragment thereof, or variant thereof that is not 100% identical to a naturally occurring OPAA.

Compositions including an effective amount of OPAA to increase hydrolysis of an organophosphate are also provided. Organophosphate compounds can include, for example, acetylcholinesterase-inhibiting compounds, butyrylcholinesterase-inhibiting compounds, insecticides (malathion, parathion, diazinon, fenthion, dichlorvos, chlorpyrifos, ethion), nerve gases (soman, sarin, tabun, VX, VR), and ophthalmic agents (echothiophate, isoflurophate), and antihelmintics (trichlorfon). In some embodiments, the compositions are pharmaceutical compositions suitable for administration onto or into a subject in need thereof. Therapeutic and prophylactic methods of using the pharmaceutical compositions to increase degradation or hydrolysis of an organophosphate in a subject in need thereof are also provided. Subjects are typically those that have been exposed to an organophosphate, or who are at risk of being exposed to one. In some embodiments, the subject exhibits one or more symptoms of organophosphate exposure or poisoning and the method is effective to reduce or alleviate the symptom, for example by hydrolyzing an acetylcholinesterase-inhibiting organophosphorus in or on the subject. In specific embodiments the OPAA is administered directly or indirectly into the blood stream of the subject (e.g., by intravenous, pulmonary, intranasal, etc., administration). In some embodiments, the OPAA is administered in an effective amount to confer 2, 5, 10, 15, 20, 25, 50, 100, 500, 750, 1,000 or more $LD_{50}$s of protection against VX or VR.

Industrial and environmental compositions such as foams, sprays, and powders, and methods of use thereof to decontaminate personnel, structures, water, vehicles, equipment, and other surfaces and liquids are also provided. The methods typically include contacting the contaminated surface or liquid with an effective amount of the composition to increase degradation of a contaminating organophosphate.

DETAILED DESCRIPTION OF THE INVENTION

I. Definitions

Figure 1:
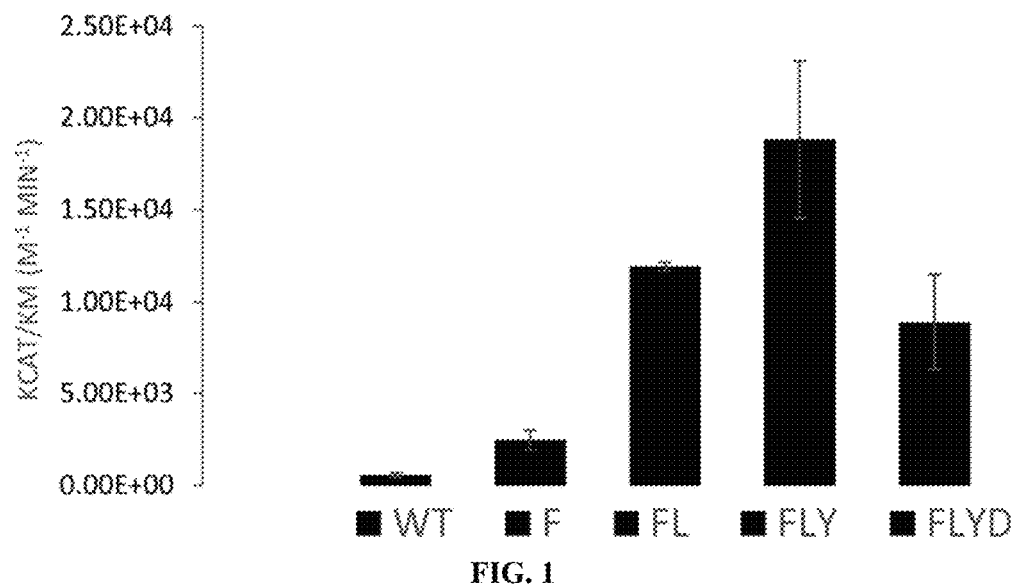
FIG. 1 is a bar graph showing OPAA $k_{cat}/K_m$ values for WT, F, FL, FLY and FLYD. All values were measured spectrophotometrically at 25° C., pH 8.0.
Figure 2:
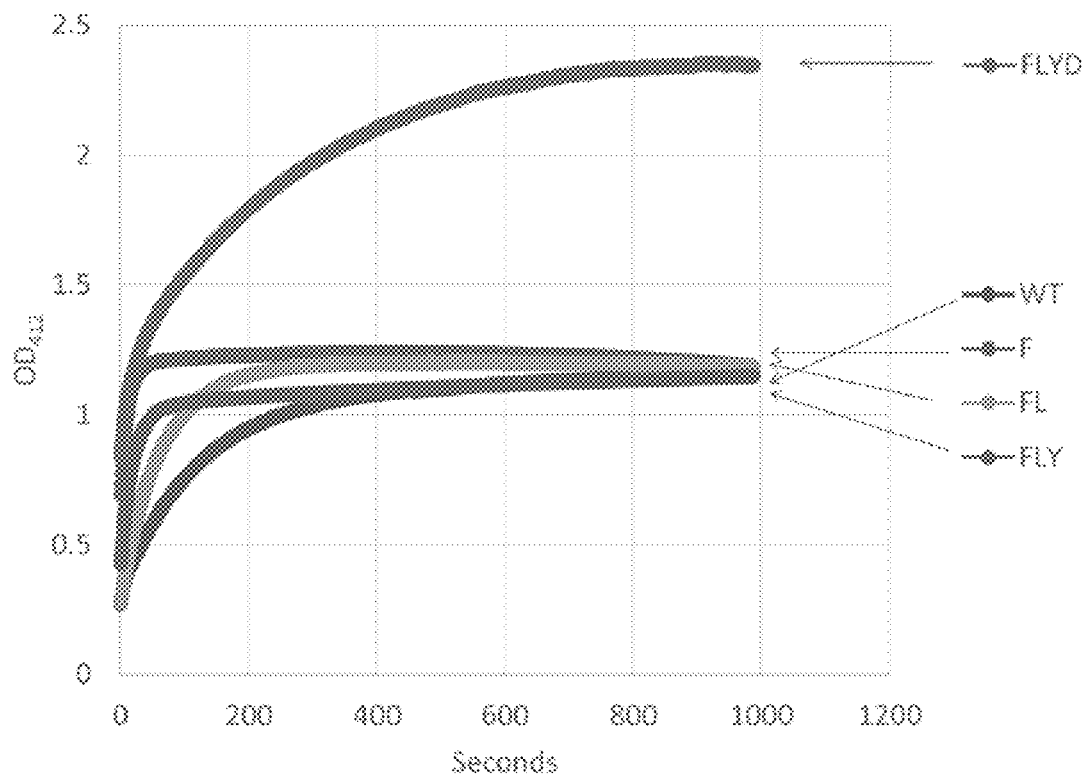
FIG. 2 is a plot showing the reaction profiles of wild-type, F, FL, FLY, and FLYD enzymes on 0.18 mM VR. Enzyme concentrations were as follows: 1.4 mg/mL WT, 2.75 mg/mL F, 0.6 mg/mL FL, 0.62 mg/mL FLY, and 1.75 mg/mL FLYD. Enzyme concentrations were selected to be roughly inversely proportional to activity.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant" polypeptide contains at least one amino acid sequence alterations as compared to the amino acid sequence of the corresponding wild-type, reference polypeptide, or naturally occurring polypeptide. An amino acid sequence alteration can be, for example, a substitution, a deletion, or an insertion of one or more amino acids, or combinations thereof.

A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides disclosed and still obtain a molecule desired characteristics (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" can also mean the degree of sequence relatedness of a polypeptide compared to the full-length of a reference polypeptide. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M, and Griffin, H. G., Eds., Humana Press, New Jersey, 1994; Sequence Analysis in Molecular Biology, von Heinje, G., Academic Press, 1987; and Sequence Analysis Primer, Gribskov, M and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and)(BLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein the term "isolated" is meant to describe a compound of interest (e.g., nucleic acids, polypeptides, etc.) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids or polypeptides are at least 60% free, preferably 75% free, and most preferably 90% free from other associated components.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. An "engineered" polypeptide is a polypeptide that was made through the hand of man and is not naturally occurring. Engineered polypeptides may have as few of one mutation (substitution, deletion, or insertion) relative to a naturally occurring polypeptide, or may have more than one mutation. The mutation(s) can introduced randomly or in a site directed fashion.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, "chiral" refers to a molecule that has a non-superposable mirror image. The feature that is most often the cause of chirality in molecules is the presence of an asymmetric carbon atom.

As used herein, "enantiomer" refers to one of two stereoisomers that are mirror images of each other that are non-superimposable (not identical).

As used herein, "enantiomeric excess" or "e.e." refers to the absolute difference between the mole fraction of each enantiomer.

As used herein, "organophosphate (OP) compounds", "organophosphorus compounds", and "organophosphates" refer to a diverse group of chemicals including an organophosphate core. Examples of organophosphates include, but is not limited to, acetylcholinesterase-inhibiting compounds, butyrylcholinesterase-inhibiting compounds, insecticides (malathion, parathion, diazinon, fenthion, dichlorvos, chlorpyrifos, ethion), nerve gases (soman, sarin, tabun, VX, VR), and ophthalmic agents (echothiophate, isoflurophate), and antihelmintics (trichlorfon).

As used herein, "VX" refers to a "V-type" nerve agent having the IUPAC name O-ethyl S-[2-(diisopropylamino) ethyl] methylphosphonothioate and having the structure:

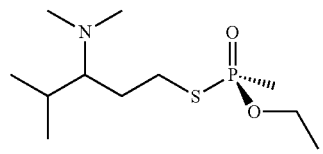 [SMILES: CCO[P@](C)(=O)SCCC(C(C)C)N(C)C]

As used herein, "VR" and "Russian VX" refers to a "V-type" nerve agent closely related (isomer) VX having the IUPAC name N,N-diethyl-2-(methyl-(2-methylpropoxy) phosphoryl)sulfanylethanamine) and having the structure:

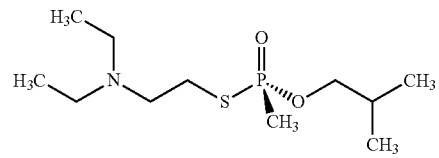 [SMILES: CCN(CC)CCS[P@](C)(=O)OCC(C)C]

As used herein, an "$LD_{50}$" or "$LD_{50}$ dose" refers to a standard measurement of acute toxicity that is stated in milligrams (mg) of organophosphate per kilogram (kg) of body weight. An $LD_{50}$ represents the individual dose required to kill 50 percent of a population of animals (e.g., humans, rats, fish, mice, cockroaches).

The term "acidic amino acid" refers to glutamic acid, aspartic acid, or combinations thereof. The amide of glutamic acid refers to glutamine. The amide of aspartic acid refers to asparagine.

II. Compositions

Genetically modified organophosphorus acid anhydrolases (OPAA) are provided. Preferred embodiments provide genetically modified OPAAs having improved catalytic efficiency or relaxed stereospecificity or both relative to unmodified OPAAs. The improved catalytic efficiency or relaxed stereospecificity is typically for one or more organophosphates including, but not limited to, acetylcholinesterase-inhibiting compounds, butyrylcholinesterase-inhibiting compounds, insecticides (malathion, parathion, diazinon, fenthion, dichlorvos, chlorpyrifos, ethion), nerve gases (soman, sarin, tabun, VX, VR), and ophthalmic agents (echothiophate, isoflurophate), and antihelmintics (trichlorfon).

A. Organophosphorus Acid Anhydrolases

Organophosphate acid anhydrolases (OPAA) are members of a class of bimetalloenzymes that hydrolyze a variety of toxic acetylcholinesterase-inhibiting organophosphorus compounds, including fluorine-containing chemical nerve agents. They also belong to a family of prolidases, with significant activity against various Xaa-Pro dipeptides. The X-ray structure of native OPAA (58 kDa mass) from *Alteromonas* sp. strain JD6.5 reveals the OPAA structure is composed of two domains, amino and carboxy domains, with the latter exhibiting a "pita bread" architecture and harboring the active site with the binuclear Mn²⁺ ions (Vyas et al., (2010) *Biochemistry* 49:547-549).

A naturally occurring OPAA was originally derived from the bacterium *Alteromonas* sp. JD6.5 and its gene has subsequently been cloned into *E. coli*. The atomic level structure of the OPAA from bacterium *Alteromonas* sp. JD6.5 is known. Although density for only 440 of the 517 amino acids were observed, truncation of the last 77 amino acids are shown not to affect enzymatic activity (DeFrank, et al., *Journal of Bacteriology*, 173:1938-1943 (1991)). U.S. Pat. No. 5,928,927 relates to the DNA sequence of an OPAA gene, its protein sequence, and a bacterial clone containing the recombinant plasmid, and clone producing an OPAA enzyme.

A consensus *Alteromonas* sp. OPAA has the amino acid sequence of:

(SEQ ID NO: 1)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDNAYGNIVALNENCAILHYTHFDRVAPATHRSFLIDAGANFN

GYAADITRTYDFTGEGEFAELVATMKQHQIALCNQLAPGKLYGELHLDCH

QRVAQTLSDFNIVDLSADEIVAKGITSTFFPHGLGHHIGLQVHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELRARLTTHSLRGLS

APQFSINDPAVMSEYSYPSEPLSYEEEIKKSTFIVHVRTRRILVRRRILS

PILIAVIPMPAITAGLM (UniProt Accession No. Q44238 - PEPQ_ALTSX,
GenBank Accession No. AAB05590.1).

In another embodiment, an OPAA has the amino acid sequence:

(SEQ ID NO: 2)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPYGNIVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQVHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELRARLTTHSLRGLS

APQFSINDPAVMSEYSYPSEPLSYEEEIKKSTFIVHVRTRRILVRRRILS

PILIAVIPMPAITAGLM.

Preferred fragments of OPAA retain enzymatic function. For example, truncation of the 77 C-terminal amino acids has been demonstrated not to diminish OPAA activity.

Accordingly, functional fragments of native OPAA include, but are not limited to, SEQ ID NO:1 without the 77 C-terminal amino acids:

(SEQ ID NO: 3)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDNAYGNIVALNENCAILHYTHFDRVAPATHRSFLIDAGANFN

GYAADITRTYDFTGEGEFAELVATMKQHQIALCNQLAPGKLYGELHLDCH

QRVAQTLSDFNIVDLSADEIVAKGITSTFFPHGLGHHIGLQVHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELRAR;

or SEQ ID NO:2 without the 77 C-terminal amino acids:

(SEQ ID NO: 4)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPYGNIVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQVHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELRAR.

In some embodiments, the mutations are relative to the functional fragment:

(SEQ ID NO: 5)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPYGNIVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQVHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELELD.

Residues that are subject of the mutations described below are bolded and underlined.

It has been discovered that OPAA can be mutated to improve its catalytic efficiency, or alter its substrate specificity, or a combination thereof. Therefore, non-naturally occurring OPAAs with improved catalytic activity, altered substrate specificity, and the combination thereof are provided. The non-naturally occurring OPAAs are referred to herein as OPAAs, engineered OPAAs, variant(s), variant OPAAs, and OPAA variants. Typically, the mutation(s) in the engineered OPAA improves the catalytic activity of OPAA for VX, VR, or both; alter or broaden the substrate specificity of OPAA to include VX, VR, or both; alter or broaden the substrate specificity of OPAA to include both stereoisomers of VX, VR, or a combination thereof; or any combination of the foregoing. As used herein, "altered substrate specificity" means to change the substrates upon which the enzyme has catalytic activity. An alteration can be an increase in the number of substrates, a decrease in the number of substrates, or both an addition and subtraction of the substrates so that net number of substrates remains the same but are different from the reference enzyme. As used herein, "broadened substrate specificity" means to increase the number of substrates. In a particularly preferred embodiment, the disclosed OPAA have an altered or broaden substrate specificity to include both stereoisomers of VX, VR, or the combination thereof.

The mutations in the disclosed OPAA can be identified relative to a reference OPAA. In some embodiments, the OPAA is a wildtype or native OPAA, a known variant, or an enzymatically active functional fragment thereof, such as the OPAA of bacterium *Altermonas* sp. or a catalytically active fragment thereof. For example, in preferred embodiments, variants have one or more amino acid mutations and typically have an amino acid sequence having at least 75%, 80%, 85%, 90%, 95%, 96%, 97%, 98%, or 99% sequence identity relative to a reference sequence such as SEQ ID NO:1, 2, 3, 4, 5, or a catalytically active fragment thereof. The mutation can be an addition, deletion, or substitution, however, the variants most typically includes at least one substitution. Functional fragments of OPAA typically include sufficient residues of OPAA to include at least the active site.

In some embodiments, the mutations in *Altermonas* sp. are made to an OPAA of a different species. OPAA from, for example, *Mycobacterium* sp.; *Amycolatopsis mediterranei; Streptomyces coelicolor; Streptomyces* sp AA4; *Streptomyces lividans* TK24; *Streptomyces sviceus* ATCC29083; *Streptomyces griseoaurantiacus* M045, are known in the art. Residues corresponding to the mutated residues in *Altermonas* sp. can be mapped and made in another species using global sequence alignment and other art-recognized methods.

The preferred mutations, Y212, V342, I215, are H343 with reference to SEQ ID NO:1-5, are disclosed individually below, however, each of the mutations is also specifically disclosed in combination with each of the others. Therefore, engineered OPAAs having one or more mutations at residues selected from the group consisting of Y212, V342, I215, and H343 are provided. In the most preferred embodiments, the engineered OPAA includes mutations at two, three, or most preferably all four positions.

The disclosed non-naturally occurring OPAA have hydrolytic activity or otherwise degrade a target substrate, however, it will be appreciated that different OPAA can have different specificities, activities, or combination thereof toward various substrates. Methods of determining activity are discussed in the Examples and known in the art. Such methods include, for example, characterization by measurements including, without limitation, western blot, marcomolecular mass determinations by biophysical determinations, SDS-PAGE/staining, HPLC and the like, antibody recognition assays, activity assays against various possible substrates illustratively including but not limited to VX, VR, or VM (N,N-diethyl-2-(methyl-(2-methylpropoxy)phosphoryl) sulfanylethanamin-e)).

The OPAA can also be characterized by substrate specificity, enantioselectivity, rate of conversion, and thermostability. In some embodiments the OPAA has an altered or broaden selectivity. For example, in the most preferred embodiments, the specificity of OPAA is expanded to include or to improve the OPAA specificity for a second stereoisomer where the reference OPAA had limited or no specificity for the second stereoisomer. Such broadening substrate specificity can be referred to broadened stereospecificity. In some embodiments the OPAA has an "N"-fold greater conversion of substrate to product over a reference OPAA such as wildtype, where "N" is an integer from 1 to 100.

Active fragments of the OPAA are also disclosed. Fragments of a full-length enzyme can retain functional activity of the enzyme, and can be referred to functional or active fragments. The fragment can be 99.5%, 99%, 98%, 97%, 96%, 95%, 85%, 80%, 75%, 70%, 60%, 50%, or less of the length of the full-length OPAA, or its full-length reference or scaffold OPAA. In some embodiments, the catalytic efficiency (e.g., $k_{cat}/K_m$) of the OPAA or functional fragment thereof is between about $10^2 M^{-1}$ min$^{-1}$ and $10^{10}$ M$^{-1}$ min$^{-1}$, or between about $10^3 M^{-1}$ min$^{-1}$ and $10^7 M^{-1}$ min$^{-1}$, or between about $10^4$ M$^{-1}$ min$^{-1}$ and $10^6 M^{-1}$ min$^{-1}$, for example, $10^2$ M$^{-1}$ min$^{-1}$, $10^3$ M$^{-1}$ min$^{-1}$, $10^4$ M$^{-1}$ min$^{-1}$, $10^5$ M$^{-1}$ min$^{-1}$, $10^6$ M$^{-1}$ min$^{-1}$, $10^7$ M$^{-1}$ min$^{-1}$, $10^8$ M$^{-1}$ min$^{-1}$, $10^9$ M$^{-1}$ min$^{-1}$, $10^{10}$ M$^{-1}$ min$^{-1}$ for a particular substrate.

Amino acid sequences for exemplary OPAA are provided below. The exemplary sequences can have 1, 2, 3, 4, 5, 6, 7, 8, 9, 10, or more additional or fewer amino acids on the N-terminus or C-terminus. For example, the amino acid sequences for the OPAA are all specifically disclosed both with and without an N-terminal methionine. The amino acid sequences can also include additional sequences to enhance expression or purification of expressed protein. For example, the amino acid sequences can optionally include a leader sequence to enhance secretion, or a purification tag to facilitate purification. The additional sequences can be added to the N-terminal or C-terminal end of the amino acid sequences provided below.

1. Engineered OPAAs with Broadened Stereospecificity

The engineered OPAA most typically include a substitution at an amino acid residue corresponding to position H343 of SEQ ID NO:1, 2, 3, 4, or 5. It has been discovered that H343D, and/or equivalent alteration in an OPAA will relax its stereospecificity allowing the resulting modified OPAA to process significantly both enantiomers of V-agents, or to increase OPAA activity towards the Sp/P(−) enantiomer of V-agents, or the combination thereof. Thus, in some embodiments, a genetically engineered OPAA polypeptide has broadened substrate specificity relative to an unmodified OPPA polypeptide by replacing at least one basic amino acid within the small pocket of the OPAA to an acidic amino acid under physiological conditions.

The Examples below illustrate that wildtype OPAA and engineered OPAAs enzymes with substitutions at Y212, V342, I215 or a combination thereof, all exhibit an almost absolute specificity for the P(+) enantiomer of VR. However, engineered OPAAs where the histidine at position 343 is replaced by an Aspartic acid (D) can have broaden substrate specificity that includes both the P(+) and P(−) enantiomers of VR, particularly when in combination with a Y212F or Y212V mutation, a V342C, V342I, V342W, V342Y, or V342L mutation, and a I215Y, I215H, or I215F, which are discussed in more detail below. The Examples illustrate that H343D, and/or equivalent alterations in an OPAA, when combined with the "FLY" to form "FLYD"

significantly increase (~16-fold) OPAA's processing of both enantiomers, or increase OPAA activity towards the Sp/P(−) enantiomer of V-agents.

Therefore, the engineered OPAAs can include mutation of H343 of SEQ ID NO:1, 2, 3, 4, or 5, or a catalytically active fragment thereof. Preferably the H343 is substituted; more preferably H343 is substituted with an acidic amino acid, for example, Aspartate (aspartic acid) or Glutamate (glutamic acid), or their amide Asparagine, Glutamine; most preferably H343 is substituted with Aspartate (aspartic acid, "D"). In preferred embodiments, the engineered OPAA also includes Y212 substituted with F or V, optionally V342 substituted with C, I, W, Y, or L, and optionally I215 substituted with Y, H, or F.

2. Engineered OPAAs with Improved Catalytic Efficiency a. Y212

The engineered OPAAs can include a substitution at an amino acid residue corresponding to position Y212 of SEQ ID NO:1, 2, 3, 4, or 5. A Y212F variant where a tyrosine (Y) is replaced by a phenylalanine (F) at position 212 of SEQ ID NO:5 has improved catalytic activity for VX and is disclosed in U.S. Pat. No. 9,017,982. U.S. Pat. No. 9,017,982 also discloses substitution of Y212 with G, F, P, Q, or T. The Examples below illustrate that Y212F, and Y212 where a tyrosine (Y) is replaced by a valine (V) at position 212 of SEQ ID NO:5 both have improved catalytic activity for VR.

Therefore, in some embodiments, the engineered OPAA includes Y212 of SEQ ID NO:1, 2, 3, 4, or 5, or a catalytically active fragment thereof, substituted with F, V, G, F, P, Q, or T; more preferably F, or V; most preferably F.

b. V342

The engineered OPAAs can include a substitution at an amino acid residue corresponding to position V342 of SEQ ID NO:1, 2, 3, 4, or 5. Engineered OPAAs where the valine at position 342 is replaced by a cysteine (C), isoleucine (I), tryptophan (W), tyrosine (Y), or leucine (L) can have improved catalytic activity for VR, particularly when in combination with a Y212F or Y212V mutation.

Therefore, in some embodiments, the engineered OPAA includes V342 of SEQ ID NO: 1, 2, 3, 4, or 5, or a catalytically active fragment thereof, substituted with C, I, W, Y, or L, most preferably L. In preferred embodiments, the engineered OPAA also includes Y212 substituted with F or V.

c. I215

The engineered OPAAs can include a substitution at an amino acid residue corresponding to position I215 of SEQ ID NO:1, 2, 3, 4, or 5. Engineered OPAAs where the isoleusine at position 215 is replaced by a tyrosine (Y), histidine (H), or phenylalanine (F) can have improved catalytic activity for VR, particularly when in combination with a Y212F or Y212V mutation, and a V342C, V342I, V342W, V342Y, or V342L mutation.

Therefore, in some embodiments, the engineered OPAA includes I215 of SEQ ID NO:1, 2, 3, 4, or 5, or a catalytically active fragment thereof, substituted with Y, H, or F, preferably Y. In preferred embodiments, the engineered OPAA also includes Y212 substituted with F or V, and optionally V342 substituted with C, I, W, Y, or L.

3. Exemplary Engineered OPAAs

In some embodiments engineered OPAAs have a sequence including:

(SEQ ID NO: 6)

MNKLAVLYAEHIATLQKRTREIIERENLDGVVFHSGQAKRQFLDDMYYPF
KVNPQFKAWLPVIDNPHCWIVANGTDKPKLIFYRPVDFWHKVPDEPNEYW

-continued

ADYFDIELLVKPDQVEKLLPYDKARFAYIGEYLEVAQALGFELMNPEPVM
NFYHYHRAYKTQYELACMREANKIAVQGHKAARDAFFQGKSEFEIQQAYL
LATQHSENDTP(Y/V/G/F/P/Q/T)GN(I/Y/H/F)VALNENCAILHYT
HFDRVAPATHRSFLIDAGANFNGYAADITRTYDFIGEGEFAELVATMKQH
QIALCNQLAPGKLYGELHLDCHQRVAQTLSDFNIVNLSADEIVAKGITSI
FFPHGLGHHIGLQ(V/C/I/W/Y/L)DDVGGFMADEQGAHQEPPEGHPFL
RCTRKIEANQVFTIEPGLYFIDSLLGDLAAIDNNQHINWDKVAELKPFGG
IRIEDNIIVHEDSLENMTRELELD, or a enzymatic or catalytic fragment thereof, wherein the OPAA is not 100% identical to SEQ ID NO:1, 2, 3, 4, or 5 or the corresponding fragment thereof. In preferred embodiments, position 212 is G, F, P, Q, or T, most preferably F. The H343D mutation in SEQ ID NO:6 is bolded and underlined.

In some embodiments engineered OPAAs have a sequence including:

(SEQ ID NO: 12)

MNKLAVLYAEHIATLQKRTREIIERENLDGVVFHSGQAKRQFLDDMYYPF
KVNPQFKAWLPVIDNPHCWIVANGTDKPKLIFYRPVDFWHKVPDEPNEYW
ADYFDIELLVKPDQVEKLLPYDKARFAYIGEYLEVAQALGFELMNPEPVM
NFYHYHRAYKTQYELACMREANKIAVQGHKAARDAFFQGKSEFEIQQAYL
LATQHSENDTP(Y/V/G/F/P/Q/T)GN(I/Y/H/F)VALNENCAILHYT
HFDRVAPATHRSFLIDAGANFNGYAADITRTYDFTGEGEFAELVATMKQH
QIALCNQLAPGKLYGELHLDCHQRVAQTLSDFNIVNLSADEIVAKGITSI
FFPHGLGHHIGLQ(V/C/I/W/Y/L)XDVGGFMADEQGAHQEPPEGHPFL
RCTRKIEANQVFTIEPGLYFIDSLLGDLAAIDNNQHINWDKVAELKPFGG
IRIEDNIIVHEDSLENMTRELELD, or an enzymatic or catalytic fragment thereof, wherein "X343" can be any amino acid except histidine, wherein the OPAA is not 100% identical to SEQ ID NO:1, 2, 3, 4, or 5 or the corresponding fragment thereof, and wherein the OPAA has relaxed or broadened substrate specificity relative to the corresponding sequence wherein amino acid 343 is a histidine. In particular embodiments, "X343" is an acidic amino acid, for example, aspartate (aspartic acid), glutamate (glutamic acid), asparagine, or glutamine. Thus, in some embodiments engineered OPAAs have a sequence including:

(SEQ ID NO: 14)

MNKLAVLYAEHIATLQKRTREIIERENLDGVVFHSGQAKRQFLDDMYYPF
KVNPQFKAWLPVIDNPHCWIVANGTDKPKLIFYRPVDFWHKVPDEPNEYW
ADYFDIELLVKPDQVEKLLPYDKARFAYIGEYLEVAQALGFELMNPEPVM
NFYHYHRAYKTQYELACMREANKIAVQGHKAARDAFFQGKSEFEIQQAYL
LATQHSENDTP(Y/V/G/F/P/Q/T)GN(I/Y/H/F)VALNENCAILHYT
HFDRVAPATHRSFLIDAGANFNGYAADITRTYDFTGEGEFAELVATMKQH
QIALCNQLAPGKLYGELHLDCHQRVAQTLSDFNIVNLSADEIVAKGITST

-continued

FFPHGLGHHIGLQ(V/C/I/W/Y/L)XDVGGFMADEQGAHQEPPEGHPFL

RCTRKIEANQVFTIEPGLYFIDSLLGDLAATDNNQHINWDKVAELKPFGG

IRIEDNIIVHEDSLENMTRELELD, or an enzymatic or catalytic fragment thereof, wherein "X343" can be aspartate (aspartic acid), glutamate (glutamic acid), asparagine, or glutamine, and is preferably aspartate (aspartic acid) or glutamate (glutamic acid), wherein the OPAA is not 100% identical to SEQ ID NO:1, 2, 3, 4, or 5 or the corresponding fragment thereof, and wherein the OPAA has relaxed or broadened substrate specificity relative to the corresponding sequence wherein amino acid 343 is a histidine.

Preferably the engineered OPAA includes 1, 2, 3, 4, or more substitutions relative SEQ ID NO:1, 2, 3, 4, or 5. In some embodiments, the engineered OPAA has an amino acid sequence with at least 75%, 80%, 85%, 90%, 95%, 96%, 97%, 98%, or 99% sequence identity to SEQ ID NO:6, 12, or 14 or a catalytically active fragment thereof, wherein the OPAA is not 100% identical to SEQ ID NO: 1, 2, 3, 4, or 5, or the corresponding fragment thereof. In some embodiments, the engineered OPAA includes a polypeptide having at least 75%, 80%, 85%, 90%, 95%, 96%, 97%, 98%, 99%, or 100% sequence identity to the region from amino acid residue 212 to amino acid residue 343 of SEQ ID NO:6, 12, or 14, wherein the OPAA is not 100% identical to the corresponding fragment SEQ ID NO:1, 2, 3, 4, or 5, and wherein the amino acids of SEQ ID NO:6 or 12 are present at the positions corresponding to residues 212, 342, 215, and 343 of SEQ ID NO:5 or 6.

In the most preferred embodiment, the OPAA includes the substitutions Y212F/V342L/I215Y/H343D ("FLYD") relative to SEQ ID NO: 1, 2, 3, 4, or 5. Accordingly, the engineered OPAA can have amino acid sequence including:

(SEQ ID NO: 7)
MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPFGNYVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQLDDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELELD, or an enzymatic or catalytic fragment thereof, or a variant of SEQ ID NO:7 or catalytic fragment thereof. The Y212F, V342D, I215Y, and H343D mutations in SEQ ID NO:7 are bolded and underlined. In some embodiments, the engineered OPAA has an amino acid sequence with at least 75%, 80%, 85%, 90%, 95%, 96%, 97%, 98%, or 99% sequence identity to SEQ ID NO:7 or a catalytically active fragment thereof, wherein the OPAA is not 100% identical to SEQ ID NO:1, 2, 3, 4, or 5, or the corresponding fragment thereof, and wherein the amino acids of SEQ ID NO:7 at 212, 342, 215, 343 (i.e., FLYD). In some embodiments, the engineered OPAA includes a polypeptide having at least 75%, 80%, 85%, 90%, 95%, 96%, 97%, 98%, 99%, or 100% sequence identity to the region from amino acid residue 212 to amino acid residue 343 of SEQ ID NO:7, wherein the OPAA is not 100% identical to the corresponding fragment of SEQ ID NO:1, 2, 3, 4, or 5, and wherein the amino acids of SEQ ID NO:7 are present at the positions corresponding to residues 212, 342, 215, and 343 of SEQ ID NO:7 (i.e., FLYD).

The engineered OPAA can have amino acid sequence including:

(SEQ ID NO: 15)

MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPFGNYVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQLSDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELELD, wherein "X343" can be aspartate (aspartic acid), glutamate (glutamic acid), asparagine, or glutamine, and is preferably aspartate (aspartic acid) or glutamate (glutamic acid).

In some embodiments, the activity and/or specificity of H343 mutant OPAA are compared a corresponding sequence without a mutation at H343, for example:

(SEQ ID NO: 13)

MNKLAVLYAEHIATLQKRTREIIERENLDGVVFHSGQAKRQFLDDMYYPF

KVNPQFKAWLPVIDNPHCWIVANGTDKPKLIFYRPVDFWHKVPDEPNEYW

ADYFDIELLVKPDQVEKLLPYDKARFAYIGEYLEVAQALGFELMNPEPVM

NFYHYHRAYKTQYELACMREANKIAVQGHKAARDAFFQGKSEFEIQQAYL

LATQHSENDTPFGNYVALNENCAILHYTHFDRVAPATHRSFLIDAGANFN

GYAADITRTYDFTGEGEFAELVATMKQHQIALCNQLAPGKLYGELHLDCH

QRVAQTLSDFNIVNLSADEIVAKGITSTFFPHGLGHHIGLQLHDVGGFMA

DEQGAHQEPPEGHPFLRCTRKIEANQVFTIEPGLYFIDSLLGDLAATDNN

QHINWDKVAELKPFGGIRIEDNIIVHEDSLENMTRELELD ("FLY").

4. Additional Modifications

The OPAA can be modified by conjugation to polymeric molecules, small molecules, or by fusion or attachment to other proteins. In some examples, conjugation to a polymer increases the half-life of the OPAA, for example, to promote prolonged/sustained treatment effects in a subject. In another example, the OPAA can be modified by fusion or attachment to proteins, such as immunoglobulins or immunoglobulin domains, albumins, transferrins, and transferrin receptor proteins, which also can affect an increase in stability and/or serum half-life.

Covalent or other stable attachment (conjugation) of polymeric molecules, such as polyethylene glycol (PEGylation moiety (PEG)) to the OPAA can improve biocompatibility, extend protein (and enzymatic activity) half-life in the serum within a subject, shield the protein from proteases and hydrolysis, improve biodistribution, enhance pharmacokinetics and/or pharmacodynamics, and increase water solubility.

Exemplary polymers that can be conjugated to the OPAA include natural and synthetic homopolymers, such as polyols (i.e. poly-OH), polyamines (i.e. poly-NH.sub.2) and polycarboxyl acids (i.e. poly-COOH), and further heteropolymers i.e. polymers containing one or more different coupling groups e.g., a hydroxyl groups and amine groups. Examples of suitable polymeric molecules include polymeric molecules selected from among polyalkylene oxides (PAO), such as polyalkylene glycols (PAG), including polyethylene glycols (PEG), methoxypolyethylene glycols (mPEG) and polypropylene glycols, PEG-glycidyl ethers (Epox-PEG), PEG-oxycarbonylimidazole (CDI-PEG), branched polyethylene glycols (PEGs), polyvinyl alcohol (PVA), polycarboxylates, polyvinylpyrrolidone, poly-D,L-amino acids, polyethylene-co-maleic acid anhydride, polystyrene-co-maleic acid anhydride, dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-starches and hydroxypropyl-starches, glycogen, agaroses and derivatives thereof, guar gum, pullulan, inulin, xanthan gum, carrageenan, pectin, alginic acid hydrolysates and bio-polymers.

In particular embodiments, the OPAA is PEGylated. PEGylation of therapeutics has been reported to increase resistance to proteolysis, increase plasma half-life, and decrease antigenicity and immunogenicity. Examples of PEGylation methodologies are known in the art (see for example, Lu and Felix, *Int. J. Peptide Protein Res.,* 43:127-138, 1994; Lu and Felix, *Peptide Res.,* 6:140-6, 1993; Felix et al., *Int. J. Peptide Res.,* 46:253-64, 1995; Benhar et al., *J. Biol. Chem.,* 269: 13398-404, 1994; Brumeanu et al., *J. Immunol.,* 154:3088-95, 1995; see also, Caliceti et al. (2003) *Adv. Drug Deliv. Rev.* 55(10):1261-77 and Molineux (2003) *Pharmacotherapy* 23 (8 Pt 2):3S-8S).

B. Nucleic Acid Molecules and Vectors

1. Isolated Nucleic Acids

Isolated nucleic acid sequences encoding engineered OPAAs are also disclosed. As used herein, "isolated nucleic acid" refers to a nucleic acid that is separated from other nucleic acid molecules that are present in a genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

Nucleic acids can be in sense or antisense orientation, or can be complementary to a reference sequence encoding an engineered OPAA. In some embodiments, the nucleic acid encodes SEQ ID NO:6, 7, 12, 14, or 15 a catalytically active fragment therefore, or variant thereof with at least 75%, 80%, 85%, 90%, 95%, 99%, or more sequence identity to SEQ ID NO: 6, 7, 12, 14, or 15.

Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Modifications at the base moiety can include deoxyuridine for deoxythymidine, and 5-methyl-2'-deoxycytidine or 5-bromo-2'-deoxycytidine for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoroamidite, or an alkyl phosphotriester backbone.

The coding sequence can be genetically engineered by altering the coding sequence for optimal expression in the host of interest.

2. Vectors

Nucleic acids, such as those described above, can be inserted into vectors for expression in cells. As used herein, a "vector" is a replicon, such as a plasmid, phage, or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen Life Technologies (Carlsbad, Calif.).

An expression vector can include a tag sequence. Tag sequences, are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, Conn.), maltose E binding protein and protein A.

C. Antibodies

Antibodies that specifically bind to the disclosed OPAA are also disclosed. In the most preferred embodiments, the antibody detects the disclosed OPAA, but not a naturally occurring OPAA, for example, by binding to an epitope that is masked or absent on the naturally occurring OPAA but present on the genetically engineered OPAA.

Methods of producing antibodies are well known and within the ability of one of ordinary skill in the art. For example, monoclonal antibodies (mAbs) and methods for their production and use are described in Kohler and Milstein, Nature 256:495-497 (1975); U.S. Pat. No. 4,376,110; Hartlow, E. et al., Antibodies: A Laboratory Manual, Cold Spring Harbor Laboratory Press, Cold Spring Harbor, N.Y., 1988); Monoclonal Antibodies and Hybridomas: A New Dimension in Biological Analyses, Plenum Press, New York, N.Y. (1980); H. Zola et al., in Monoclonal Hybridoma Antibodies: Techniques and Applications, CRC Press, 1982)).

The antibodies can be monoclonal or polyclonal. The antibodies may be xenogeneic, allogeneic, syngeneic, or modified forms thereof, such as humanized, single chain or chimeric antibodies. The term "antibody" is also meant to include both intact molecules as well as fragments thereof that include the antigen-binding site and are capable of binding to a B7-H4 receptor epitope. These include Fab and F(ab')$_2$ fragments which lack the Fc fragment of an intact antibody, and therefore clear more rapidly from the circulation, and may have less non-specific tissue binding than an intact antibody (Wahl et al., J. Nuc. Med. 24:316-325 (1983)). Also included are Fv fragments (Hochman, J. et al., Biochemistry, 12:1130-1135(1973); Sharon, J. et al., Biochemistry, 15:1591-1594 (1976)). These various fragments can be produced using conventional techniques such as protease cleavage or chemical cleavage (see, e.g., Rousseaux et al., Meth. Enzymol., 121:663-69 (1986)).

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography.

The immunogen may be any immunogenic portion of the OPAA. Preferred immunogens include all or a part of mutations in the engineered OPAA. Immunogens are produced in a variety of ways known in the art, e.g., expression of cloned genes using conventional recombinant methods, isolation from cells of origin, cell populations expressing high levels of OPAA or a fragment thereof.

The mAbs may be produced using conventional hybridoma technology, such as the procedures introduced by Kohler and Milstein, *Nature,* 256:495-97 (1975), and modifications thereof (see above references). An animal, preferably a mouse is primed by immunization with an immunogen as above to elicit the desired antibody response in the primed animal.

B lymphocytes from the lymph nodes, spleens or peripheral blood of a primed, animal are fused with myeloma cells, generally in the presence of a fusion promoting agent such as polyethylene glycol (PEG). Any of a number of murine myeloma cell lines are available for such use: the P3-NS1/1-Ag4-1, P3-x63-k0Ag8.653, Sp2/0-Ag14, or HL1-653 myeloma lines (available from the ATCC, Rockville, Md.). Subsequent steps include growth in selective medium so that unfused parental myeloma cells and donor lymphocyte cells eventually die while only the hybridoma cells survive. These are cloned and grown and their supernatants screened for the presence of antibody of the desired specificity, e.g., by immunoassay techniques using the B7-H4-Ig fusion protein. Positive clones are subcloned, e.g., by limiting dilution, and the mAbs are isolated.

Hybridomas produced according to these methods can be propagated in vitro or in vivo (in ascites fluid) using techniques known in the art (see generally Fink et al., *Prog. Clin. Pathol.,* 9:121-33 (1984)). Generally, the individual cell line is propagated in culture and the culture medium containing high concentrations of a single mAb can be harvested by decantation, filtration, or centrifugation.

The antibody may be produced as a single chain antibody or scFv instead of the normal multimeric structure. Single chain antibodies include the hypervariable regions from an Ig of interest and recreate the antigen binding site of the native Ig while being a fraction of the size of the intact Ig (Skerra, A. et al., *Science,* 240: 1038-1041 (1988); Pluckthun, A. et al., *Methods Enzymol.,* 178: 497-515 (1989); Winter, G. et al. *Nature,* 349: 293-299 (1991); Bird et al., *Science* 242:423 (1988); Huston et al. *Proc. Natl. Acad. Sci. USA* 85:5879 (1988); Jost C R et al, *J Biol Chem.* 269: 26267-26273 (1994); U.S. Pat. Nos. 4,704,692, 4,853,871, 4,946,778, 5,260,203. In a preferred embodiment, the antibody is produced using conventional molecular biology techniques.

Methods of using the antibodies to detect the presence of the epitope are described in Coligan, J. E. et al., eds., Current Protocols in Immunology, Wiley-Interscience, New York 1991 (or current edition); Butt, W. R. (ed.) Practical Immunoassay: The State of the Art, Dekker, N.Y., 1984; Bizollon, Ch. A., ed., Monoclonal Antibodies and New Trends in Immunoassays, Elsevier, N.Y., 1984; Butler, J. E., ELISA (Chapter 29), In: van Oss, C. J. et al., (eds), IMMUNOCHEMISTRY, Marcel Dekker, Inc., New York, 1994, pp. 759-803; Butler, J. E. (ed.), Immunochemistry of Solid-Phase Immunoassay, CRC Press, Boca Raton, 1991; Weintraub, B., Principles of Radioimmunoassays, Seventh Training Course on Radioligand Assay Techniques, The Endocrine Society, March, 1986; Work, T. S. et al., Laboratory Techniques and Biochemistry in Molecular Biology, North Holland Publishing Company, NY, (1978) (Chapter by Chard, T., "An Introduction to Radioimmune Assay and Related Techniques").

In some embodiments, the antibodies are specific for SEQ ID NO: 6, 7, 12, or 14, a catalytically active fragment therefore, or variant thereof with at least 75%, 80%, 85%, 90%, 95%, 99%, or more sequence identity to SEQ ID NO: 6, 7, 12, or 14. In some embodiments, the antibodies bind to SEQ ID NO:6, 7, 12, 14, or a combination thereof, but not one or more of SEQ ID NO:1, 2, 3, 4, 5, or 13. In a specific embodiment, the antibodies bind to SEQ ID NO:7, but not to SEQ ID NO:13.

III. Methods of Making Organophosphorus Acid Anhydrolases

A. Expression of Organophosphorus Acid Anhydrolases

The cDNA species encoding the disclosed OPAA can be expressed as encoded peptides or proteins. The engineering of DNA segment(s) for expression in a prokaryotic or eukaryotic system may be performed by techniques generally known to those of skill in recombinant expression. It is believed that virtually any expression system may be employed in the expression of the disclosed enzymes.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene.

Recombinant cells include those having an introduced cDNA or genomic DNA, and also include genes positioned adjacent to a promoter not naturally associated with the particular introduced gene.

To express a recombinant encoded protein or peptide, whether mutant or wild-type, one would prepare an expression vector that comprises one of the claimed isolated nucleic acids under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B, *E. coli* 1776 (ATCC No. 31537) as well as *E. coli* W3110 (F-, lambda-, prototrophic, ATCC No. 273325); bacilli such as *Bacillus subtilis*; and other enterobacteriaceae such as *Salmonella typhimurium*, *Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in *Saccharomyces*, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, *Autograph californica* nuclear polyhidrosis virus (AcNPV) is used as a vector to express foreign genes. The virus grows in *Spodoptera frugiperda* cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed.

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired. Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HinDIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides downstream of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The OPAA can optionally include additional sequences or moieties, including, but not limited to linkers and purification tags.

In a preferred embodiment the purification tag is a polypeptide. Polypeptide purification tags are known in the art and include, but are not limited to His tags which typically include six or more, typically consecutive, histidine residues; FLAG tags, which typically include the sequence DYKDDDDK (SEQ ID NO:8); haemagglutinin (HA) for example, YPYDVP (SEQ ID NO:9); MYC tag for example ILKKATAYIL (SEQ ID NO:10) or EQKLISEEDL (SEQ ID NO:11). Methods of using purification tags to facilitate protein purification are known in the art and include, for example, a chromatography step wherein the tag reversibly binds to a chromatography resin.

Purifications tags can be N-terminal or C-terminal to the fusion protein. The purification tags N-terminal to the fusion protein are typically separated from the polypeptide of interest at the time of the cleavage in vivo. Therefore, purification tags N-terminal to the fusion protein can be used to remove the fusion protein from a cellular lysate following expression and extraction of the expression or solubility enhancing amino acid sequence, but cannot be used to remove the polypeptide of interest. Purification tags C-terminal to the fusion protein can be used to remove the polypeptide of interest from a cellular lysate following expression of the fusion protein, but cannot be used to remove the expression or solubility enhancing amino acid sequence. Purification tags that are C-terminal to the expression or solubility enhancing amino acid sequence can be N-terminal to, C-terminal to, or incorporated within the sequence of the polypeptide of interest.

In some embodiments, to fusion protein includes one or more linkers or spacers. In some embodiments linker or spacer is one or more polypeptides. In some embodiments, the linker includes a glycine-glutamic acid di-amino acid sequence. The linkers can be used to link or connect two domains, regions, or sequences of the fusion protein.

It is contemplated that the isolated nucleic acids of the invention may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Although many proteins with therapeutic or commercial uses can be produced by recombinant organisms, the yield and quality of the expressed protein are variable due to many factors. For example, heterologous protein expression by genetically engineered organisms can be affected by the size and source of the protein to be expressed, the presence of an affinity tag linked to the protein to be expressed, codon biasing, the strain of the microorganism, the culture conditions of microorganism, and the in vivo degradation of the expressed protein. Some of these problems can be mitigated by fusing the protein of interest to an expression or solubility enhancing amino acid sequence. Exemplary expression or solubility enhancing amino acid sequences include maltose-binding protein (MBP), glutathione S-transferase (GST), thioredoxin (TRX), NUS A, ubiquitin (Ub), and a small ubiquitin-related modifier (SUMO).

In some embodiments, the compositions disclosed herein include expression or solubility enhancing amino acid sequence. In some embodiments, the expression or solubility enhancing amino acid sequence is cleaved prior administration of the composition to a subject in need thereof. The expression or solubility enhancing amino acid sequence can be cleaved in the recombinant expression system, or after the expressed protein in purified. In some embodiments, the expression or solubility enhancing is a ULP1 or SUMO sequence. Recombinant protein expression systems that incorporate the SUMO protein ("SUMO fusion systems") have been shown to increase efficiency and reduce defective expression of recombinant proteins in *E. coli*, see for example Malakhov, et al., *J. Struct. Funct. Genomics*, 5: 75-86 (2004), U.S. Pat. No. 7,060,461, and U.S. Pat. No. 6,872,551. SUMO fusion systems enhance expression and solubility of certain proteins, including severe acute respiratory syndrome coronavirus (SARS-CoV) 3CL protease, nucleocapsid, and membrane proteins (Zuo et al., *J. Struct. Funct. Genomics*, 6:103-111 (2005)).

B. Purification of Expressed Proteins

Composition and methods for purification, or the substantial purification, of an encoded protein or peptide are also disclosed. The term "purified protein or peptide" as used herein, is intended to refer to a composition, isolatable from other components, wherein the protein or peptide is purified to any degree relative to its naturally-obtainable state, i.e., in this case, relative to its purity within a hepatocyte or p-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

In particularly embodiment, the OPAA was prepared by the procedures adapted from U.S. Pat. Nos. 5,928,927 and 6,080,566, which are each specifically incorporated by reference herein in their entirety.

IV. Formulations

Compositions including OPAA are also disclosed. The compositions can be formulated for environmental or industrial use or administration directly to a subject in need thereof. The disclosure of pharmaceutical compositions below, does not preclude them from use in industrial and environmental settings, therefore the compositions disclosed for pharmaceutical use are also specifically disclosed for environmental or industrial use. In some embodiments, the composition includes $MnCl_2$ for enhanced stability. Preferred formulations for decontamination application are discussed in more detail below.

A. Pharmaceutical Compositions

Pharmaceutical compositions including an OPAA are provided. Pharmaceutical compositions can be for administration by parenteral (intramuscular, intraperitoneal, intraarterial, intravenous (IV)) or subcutaneous injection), pulmonary, or transmucosal (nasal, vaginal, rectal, or sublingual) routes of administration or using bioerodible inserts and can be formulated in dosage forms appropriate for each route of administration. In some preferred embodiments for therapeutic or prophylactic treatment, the OPAA is delivered into the blood stream of the subject by, for example, intravenous injection or infusion, or an intranasal or pulmonary delivery method. In some embodiments, the compositions are delivered topically.

In certain embodiments, the compositions are administered locally, for example by injection or topically application directly into a site to be treated. The compositions are preferably administered systemically.

1. Formulations for Parenteral Administration

Compositions including those containing an OPPA can be administered in an aqueous solution, by parenteral injection. The formulation may also be in the form of a suspension or emulsion. In general, pharmaceutical compositions are provided including effective amounts of the OPAA and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Pulmonary and Intranasal Delivery

The OPAA can be applied topically. Topical administration can include application to the lungs, nasal, oral (sublingual, buccal), vaginal, or rectal mucosa, and to the skin.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

B. Delivery Vehicles

The OPAA is optionally delivered as naked polypeptide, in aqueous solution, in an emulsion, or in other suitable delivery composition. In some embodiments, the invention is delivered as a component of a pharmaceutical package. Optionally, a protein (or multiple proteins) is present in an emulsion including one or more emulsification agents. In some embodiments, a non-wild-type OPAA is emulsified. In some embodiments, the delivery vehicle is incorporated into or encapsulated by a nanoparticle, microparticle, micelle, synthetic lipoprotein particle, or carbon nanotube. Suitable emulsification agents illustratively include supramolecular biovectors (SMBV). Liposomes such as described by El Guink et al., Vaccine, 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally the adjuvant is monophosphoryl lipid A.

Suitable nanoparticles include those described by Major, M. et al, *Biochim. Biophys. Acta,* 1997; 1327:32-40, De Migel, I, et al, *Pharm. Res.,* 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et el, *Vaccine,* 1996; 14:1353-1360, Prieur, E., et al, *Vaccine,* 1996; 14:511-520, Baudner B, et al, *Infect Immun,* 2002; 70:4785-4790. In some embodiments, a vehicle such as polymeric microparticles provide controlled release of the OPAA. In some embodiments, release of the drug(s) is controlled by diffusion of the OPAA out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

Particularly preferred compositions and methods for nanoecapsulation of OPAA are disclosed in U.S. Pat. No. 6,716,450, which is specifically incorporated by reference herein in its entirety.

V. Methods of Use

Methods of reducing the level or activity of an organophosphate are provided. The methods include contacting the organophosphate with an OPAA. The organophosphate compound can be, for example, a acetylcholinesterase-inhibiting compound, butyrylcholinesterase-inhibiting compound, insecticide (malathion, parathion, diazinon, fenthion, dichlorvos, chlorpyrifos, ethion), nerve gas (soman, sarin, tabun, VX, VR), and ophthalmic agent (echothiophate, isoflurophate), and antihelmintics (trichlorfon). The methods can be employed in therapeutic, prophylactic, environmental, and industrial applications.

A. Methods of Treatment

1. Therapeutic and Prophylactic Methods

Methods of treating or inhibiting organophosphorus poisoning in a subject are provided. The methods typically include administering to the subject an effective amount of an OPAA to reduce the level or activity of an organophosphate in or on the subject. In a particular embodiment, the method includes hydrolyzing VX, VR, or a combination thereof in a subject exposed to VX, VR, or a combination thereof by administering to the subject an effective amount of an OPAA. In some embodiments, the OPAA is administered in an effective amount to reduce one or more symptoms of organophosphate exposure or poisoning. Symptoms include, but are not limited to, myopathy, psychosis, general paralysis, twitching, trembling, paralyzed breathing, convulsions, miosis, blurred vision, dark vision, headache, nausea, dizziness, vomiting, hypersecretion, sweating, salivation, lacrimation, rhinorrhea, abdominal cramps, diarrhea, urinary incontinence, muscle twitching/fasciculations, paralysis, pallor, muscle weakness, tremors, convulsions, incoordination, diaphoresis, bronchospasm, bronchorrhea, tightness in chest, wheezing, productive cough, pulmonary edema, bradycardia, sinus arrest, tachycardia, hypertension, toxic myocardiopathy, mydriasis, ataxia, anxiety, restlessness, choreiform movement, loss of consciousness, respiratory depression, fatigue, seizures, depression, memory loss, confusion, and combinations thereof.

In particular embodiments, a pharmaceutical formulation suitable for intravenous injection or infusion can include an effective amount of an OPAA to reduce the level or activity of an organophosphate when injected into a subject whose has been exposed to the organophosphate.

2. Subjects to be Treated

The OPAA typically hydrolyzes or otherwise degrades the organophosphate in or on the subject. Therefore, the OPAA can be administered therapeutically to a subject that has been exposed to or ingested an organophosphate. The OPAA can also be administered prophylactically to a subject that is at risk of being exposed to an organophosphate prior to exposure. Examples of suitable subjects include, but are not limited to, civilians contaminated by a terrorist attack at a public event, individuals exposed to accidental spills in industry and during transportation, field workers subjected to pesticide or insecticide organophosphorus poisoning, truckers who transport pesticides, pesticide manufacturers, dog groomers who are overexposed to flea dip, pest control workers various domestic and custodial workers who use organophosphorus compounds and military personnel exposed to nerve gases. In particularly embodiments, the subjects were exposed to or in danger of being exposed to a V-type nerve agent such as VX or VR.

3. Dosages

Dosage of the OPAA will depend on the condition of the subject and the activity of the enzyme. In some embodiments, an effective amount can be between about 0.05 to about 1000 µg/mL of OPAA. A suitable dosage may be about 1.0 mL of such an effective amount. Such a composition may be administered, for example, 1-3 times per day over a 1 day to 12 week period. However, suitable dosage adjustments may be made by the attending physician or veterinarian depending upon the age, sex, weight and general health of the subject. Such a composition is optionally administered parenterally, optionally intramuscularly or subcutaneously. However, it may also be formulated to be administered by any other suitable route. In some embodiments, the OPAA is administered in an effective amount to confer between about 2 and 1000, or between 5 and 500, or between 10 and 200, or between 15 and 50 $LD_{50}$ doses of protection against an organophosphate. For example, in some embodiments the OPPA confers 2, 5, 10, 15, 20, 25, 50, 100, 500, 750, or 1,000 $LD_{50}$s of protection against an organophosphate, preferably VX or VR.

The pharmaceutical compositions can be formulated as a pharmaceutical dosage unit, also referred to as a unit dosage form. Dosage units can include an effective amount of OPAA for a single administration.

4. Combination Therapies

In some embodiments, the OPAA are administered in combination with one or more additional agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft.

In particular embodiments, the additional agent or agents are also for treatment for organophosphate exposure. Exemplary agents include, but are not limited to, atropine, pralidoxime (2-PAM), and benzodiazepines (e.g., diazepam). Glycopyrrolate, diphenhydramine, and magnesium therapy have also been used to treat organophosphate poisoning.

B. Methods of Decontamination

Methods of decontaminating or detoxifying a surface or liquid exposed to an organophosphate are also provided. The methods typically include contacting the contaminated surface or liquid with an effective amount of OPAA to reduce the level or activity of the organophosphate. In some embodiments, the method is employed to protect a surface or liquid in danger of being exposed to an organophosphate. The OPAA can be administered to the surface or liquid using any suitable means. For example, the OPAA can be sprayed or coated on the surface or liquid. In some embodiments, the OPAA is incorporated with a foam, wetting agent or degreaser prior to application to aid in the application of the composition and solubilization of organophosphorus compounds. The resulting mixture can be applied to the surface to be decontaminated either manually or with a foam or spray system. Foam and spray systems are uncomplicated and have been used extensively for fire-fighting operations for many years.

Applying the OPAA composition with foam offers the advantage that the foam would act as a "blanket" to retard evaporation and shield the enzyme from inhibitory environmental elements. In addition, foam could also stabilize the enzyme and thus prolong its activity in the field. Because this foam-based detoxification system would not jeopardize user safety or harm the environment, it could be applied topically to personnel, equipment, agricultural fields or other large areas contaminated with OP compounds.

The OPAA can a dried powder (e.g., lyophilized) or in a solution, suspension, emulsion, etc. In some embodiments, the composition is prepared as a dry powder and reconstituted with various water sources when needed. In some embodiments, the composition is viscous, includes a bonding agent, or a combination thereof to enhance the duration of contact between the OPAA and the treated surface. The composition can include, or be used in conjunction with a reducing agent such dithiothreitol (DTT) or beta-mercaptoethanol which can enhance OPAA activity. In some embodiments, the ambient temperature is maintained between about 10° C. and 65° C. and/or the ambient pH is between about 6.5 and 9.5 to enhance enzyme stability and activity. In some embodiments, the OPAA is in a composition that has a pH is between about 6.5 and 9.5. The enzyme is unstable under harsh conditions, losing its activity in the presence of organic solvents, at elevated temperature, and over long-term storage, accordingly, such conditions are typically avoided when possible. U.S. Pat. No. 6,080,566, which is specifically incorporated by reference herein in its entirety, relates to OPAA assay composition, use of OPAA in different carriers such as foams, degreasers, wetting agents, lyophilization for producing powder enzyme, and method for degrading OP compounds, including G-type agents, which can be adapted for use with the OPAA disclosed herein.

Treatable surfaces including, but are not limited to, vegetation, organisms including humans and other animals, clothing, soil, buildings and other structures, vehicles, and equipment. Treatable liquids include, but are not limited to, water, including ground water. In some embodiments, the OPAA is used to decontaminate agricultural equipment, remediate contaminated soils, and treat waste water generated from production facilities.

Other compositions for decontamination using OPAA and methods of use thereof disclosed in U.S. Pat. No. 7,723,558 and can be adapted for use with the disclosed OPAA. For example, suitable compositions include, fire-fighting foams, degreasers, laundry detergent, skin lotion, and other matrices. The catalytic activity of wildtype OPAA is enhanced in the presence of several water-soluble and biodegradable commercial agents, degreasers, and foams, e.g. COLD-FIRE®, ODOR SEAL®, TIDE-FREE®, and CORN-SOLV®, retained in the presence of Fire Choke, and also quite active in other fire-fighting agents, AFC-380®, BIO-SOLVE®, and BV 406LF®. The incorporation of these biodegradable matrices with the enzyme decontamination system not only provides a medium to encapsulate the contaminating agent, but also assists in solubilization of the agent for enzyme action.

Additional materials, compositions, kits and methods for neutralizing, detoxifying or decontaminating equipment and/or personnel suitable for use with OPAA are disclosed in U.S. Pat. No. 6,541,230, which is specifically incorporated by reference herein in its entirety.

Methods of detecting organophosphate contamination of a surface or liquid and methods of measuring the rate of decontamination of a surface or liquid with organophosphate are also provided. The methods can include contacting the surface or liquid with an effective amount of an OPAA and detecting a product of catalysis. Products and by-products of OPAA catalysis are known in the art and depend on the organophosphate substrate. Such products can be detected using any suitable method known in the art, including biochemical means of detection or analytical chemistry, for example HPLC.

VI. Kits

Kits including an OPAA are also provided. Components of the kit may be packaged individually and can be sterile. In some embodiments, a pharmaceutically acceptable carrier containing an effective amount of OPAA is shipped and stored in a sterile vial. In other embodiments the OPAA is dried, lyophilized powder, and the kit includes a buffer or other pharmaceutical carrier for reconstituting the OPAA. The sterile vial may contain enough OPAA for one or more doses. OPAA may be shipped and stored in a volume suitable for administration, or may be provided in a concentrated titer that is diluted prior to administration. In another embodiment, a pharmaceutically acceptable carrier containing an effective amount of OPAA is shipped and stored in a syringe. In a particular embodiment the OPAA and carrier are stored separately in a syringe and the OPAA is reconstituted in the syringe before administration to the subject.

Kits containing syringes of various capacities or vessels with deformable sides (e.g., plastic vessels or plastic-sided vessels) that can be squeezed to force a liquid composition out of an orifice are provided. The size and design of the syringe will depend on the route of administration. In some embodiments, a large syringe, pump or catheter is used to administer virus systemically. Any of the kits can include instructions for use.

EXAMPLES

Daczkowski, et al., *Engineering the Organophosphorus Acid Anhydrolase Enzyme for Increased Catalytic Efficiency and Broadened Stereospecificity on Russian VX*, Biochemistry, 54(41):6423-6433 (2015), DOI: 10.1021/acs.biochem.5b00624, as well as all supplemental information associated therewith including but not limited to text, tables, and figures, are specifically incorporated by reference herein it their entireties.

Abbreviations: ALS, Advanced Light Source; CASARM, Chemical Agent Standard Analytical Reference Material; DDP, N,N'-Diisopropyldiamidophosphate; DFP, Diisopropylfluorophosphate; DSSP, Definition of Secondary Structure of Proteins; OPAA, Organophosphorus Acid Anhydrolase; PISA, Proteins, Interfaces, Structures and Assemblies; PTE, Phosphotriesterase Enzyme; VR, Russian VX, O-isobutyl S-[2-(diethylamino)ethyl] methylphosphonothioate; VX, O-ethyl S-[2-(diisopropylamino)ethyl] methylphosphonothioate Example 1

Engineered OPAA have Increased Enzymatic Activity for VR Chemical Agent

Materials and Methods

Materials

Chemical agent substrates were obtained from Edgewood Chemical Biological Center stocks and were Chemical Agent Standard Analytical Reference Materials, typically of greater than 95% purity. Chemicals, biochemicals, buffers and solvents were purchased from Sigma-Aldrich Chemical Co. (St. Louis, Mo.), Fisher Scientific, Inc. (Pittsburgh, Pa.), or Acros Organic (Morris Plains, N.J.), unless otherwise indicated. 5,5'-dithio-bis(2-nitrobenzoic acid) (DTNB, CAS-69-78-3) was purchased from Sigma, item number D8130, lot number 54H0479. Ethyl acetate (CAS 141-78-6) was purchased from Aldrich, item number 11,0002-7, lot number 143110BZ. Bis-tris-propane (CAS 66431-96-5) was purchased from Sigma, item number B6755-1KG, lot number SLBD7878V. $MnCl_2$ (CAS 13446-34-9) was purchased from Sigma, item number M-3634-100G, lot number 111K0151.

OPAA Expression Vector and Site-directed Mutagenesis of the OPAA Gene

The gene encoding the OPAA enzyme was originally cloned from *Alteromonas* sp. JD6.5, as described (Cheng, et al., *Applied and Environmental Microbiology*, 62:1636-1641 (1996)). The OPAA gene utilized is a naturally occurring variant. It differs from previous OPAA entry Q44238.3 by three amino acids at sites 210, 211, and 314. The present gene, which was modified by site-directed mutagenesis, lacks the last 77 carboxyl-terminus amino acids of the OPAA enzyme, and has an amino acid sequence according to SEQ ID NO:5 (provided above). This truncated gene was cloned into the NcoI and the EcoRI sites of the pSE420 expression vector of *E. coli*. The resulting mutant plasmids were introduced into *E. coli* BL21 (DE3) competent cells by electroporation and were typically grown to late log phase in 1 L flasks without induction to produce enzyme. The complete coding regions for all mutant enzymes were sequenced by DNA2.0 (www.dna20.com).

Production and Purification of Engineered OPAAs

The engineered OPAA enzymes were prepared by a method similar to that described previously for OPAA (Cheng, et al., *Applied and Environmental Microbiology*, 62:1636-1641 (1996)). Briefly, the cells were harvested and centrifuged and the proteins from the supernatant were precipitated in 65% ammonium sulfate. This pellet was resuspended in 13 mL of 10 mM bis-tris-propane, pH 8.0 with 0.1 mM $MnCl_2$ and passed through a size exclusion column. The active fractions were pooled and loaded on a 10 ml Q Sepharose column and eluted with a 0.2-0.6 M NaCl gradient. The active fractions from the Q Sepharose column were pooled, precipitated in 65% ammonium sulfate, resuspended in and dialyzed against 10 mM bis-tris-propane, pH 8.0 with 0.1 mM MnCl2. The resulting protein migrated with apparent homogeneity on SDS-PAGE.

VR Enzymatic Assays

The kinetic constants were determined by spectrophotometry using 0.3 mM DTNB) in 50 mM bis-tris-propane buffer, pH 8.0 and 0.1 mM $MnCl_2$ at 25° C. in a 1 mL cuvette with a total sample volume of 0.5 mL. Samples were monitored at 412 nm typically for five minutes and activity was calculated using an extinction coefficient of 14,150 $M^{-1}$ $cm^{-1}$. The assay measured the concentration of free thiol from the enzyme-catalyzed cleavage of the P—S bond of VR. VR samples were Chemical Agent Standard Analytical Reference Material (CASARM) and were of the highest purity available, typically 99.9+/−5.4 weight % by oxidation-reduction titration, traceable to National Institute of Standards and Technology through 0.1 N iodine solution SRM 136e. Kinetic parameters were calculated using Biosoft EnzFitter© software (Biosoft.com). Activity data were generally collected at substrate concentrations ranging from ⅓ to three times the Km under conditions that consumed less than 10% of the substrate. At least five different substrate concentrations were used for each determination.

Single isomer isolates for polarimetry were prepared from a 900 mL solution of 50 mM bis-tris-propane buffer pH 8.0 containing 0.5 mM substrate. In order to facilitate rapid dissolution, the substrates were diluted into 1 mL isopropyl alcohol prior to addition to the buffer. The solution was brought to 35° C. and the reaction was initiated with the addition of 0.93 μg/mL of enzyme. Reaction progress was monitored spectrophotometrically and when the product concentration had just exceeded the remaining VR concentration (i.e. the point at which the preferred isomer would be essentially completely hydrolyzed), the reaction was stopped by plunging it into a slushy ice bath and extracting twice with 50 mL ethyl acetate, shaking vigorously each time. The organic layer was removed, concentrated to approximately 1 mL by rotary evaporation, and used for polarimetry in an Anton Paar MCP 500 instrument.

Crystallization of Engineered OPAAs

Initial crystal conditions for OPAA Y212F were determined from high-throughput screening of Qiagen Nextel Screens, Classics, Classics II, PEGs, PEGs II, Anion, Cation, PhClear I, and PhClear II suites, in a 96 well hanging drop format using a TTP Mosquito Crystal liquid handling robot. Drops contained 150 nL of protein solution to 150 nL of precipitate. Reservoir volume with a 100-μL reservoir volume. Initial screening resulted in crystals from conditions with 10% PEG 4,000, 20% isopropanol and 8.5 mg/mL of OPAA Y212. However, utilizing a gradient screen of PEG 4,000 and isopropanol screening precipitant conditions containing 4% PEG 4,000 and 20% Isopropanol produced the most viable crystals. These crystals were optimized using the Additive HT Screen from Hampton Research. Final OPAA Y212F crystals were obtained through hanging-drop vapor diffusion at 20° C. and included using a 500-μL reservoir with 2-μL hanging drops mixed 1:1 with protein solution and 0.25 μL of 0.1 M BaCl2. Crystal conditions for OPAA FLY crystals were obtain under the same conditions. For co-crystals of OPAA Y212F and mipafox, the mipafox was added to the OPAA protein solution to a final concentration of 790 uM prior to crystallization was used.

Results

Kinetic analysis of the wild-type enzyme on VR showed a $k_{cat}/K_m$ value of approximately $2.48\times10^2 M^{-1}$ $min^{-1}$, a rate probably four orders of magnitude too slow to be effective as a medical countermeasure (Table 1). The OPAA substrate-binding site is composed of a small pocket, a large pocket, and a leaving group pocket. The large pocket is formed by Leu225, His226, His332, and Arg418. The leaving group pocket is composed of Tyr292 and Leu366. The small pocket is formed by residues Tyr212, Val342, His343, and Asp45 from the N-terminal domain of the opposite subunit in the dimer. All three pockets are in close proximity to the binuclear active site.

Attempts to increase the size of the leaving group site through mutation of Tyr292 proved to be unsuccessful. Twelve individual mutants (A, D, F, G, H, I, K, L, P, R, S, and V) were expressed and purified but no significant increase in 3 mM VR activity was observed from substitution of any of these amino acids. This indicated that enlargement of the leading group to facilitate the larger VR molecule, as compared to GD, for instance, may not be a practical way forward towards increasing VR activity within OPAA.

As the larger pocket is already significantly large enough to accommodate the side chains of VR, the focus for optimization of OPAA was placed on the small pocket. Initially, Tyr212 was selected for mutagenesis as its ring system forms one of the small pocket walls. Subsequently, all amino acids except isoleucine were substituted into the Tyr212 site. Individual mutants were purified and assayed on 3 mM VR. Intriguingly, OPAAs containing the Y212F, or Y212V substitutions demonstrated a significant increase in activity towards 3 mM VR. As one of the more active mutants, OPAA Y212F underwent full kinetic analysis. Its $k_{cat}$ was five times higher than truncated wild-type OPAA, while its $K_M$ remained largely remained unchanged. This translated into a roughly five times higher catalytic efficiency than truncated wild-type OPAA (Table 1, FIG. 1).

TABLE 1

Genotypes and kinetic parameters of purified OPAA enzymes.

| Enzyme | Genotype | $k_{cat}$ (min$^{-1}$) | +/− | Km (μM) | +/− | $k_{cat}$/Km (M$^{-1}$ min$^{-1}$) | +/− |
|---|---|---|---|---|---|---|---|
| WT | Wild-type | 1.8 | 0.12 | 3280 | 551 | 548 | 128 |
| F | Y212F | 11 | 0.75 | 4482 | 680 | 2451 | 540 |
| FL | Y212F/V342L | 21 | 1.1 | 1767 | 258 | 11894 | 2349 |
| FLY | Y212F/V342L/I215Y | 38 | 2.7 | 1915 | 456 | 19642 | 6071 |
| FLYD | Y212F/V342L/I215Y/H343D | 18 | 1.3 | 2075 | 460 | 8890 | 258 |

Example 2

Crystallization of Engineered OPAAs

Materials and Methods

X-Ray Structure of Engineered OPAAs

X-ray data sets were collected using crystals mounted onto polymer loops (Mitegen) and flash-cooled in liquid nitrogen. All crystals were passed through a cryo of 20% isopropanol, 15% PEG 4,000, and 5% Glycerol before being mounted under a stream of dry N2 at 100 K. Collections for all data sets used an X-ray beam wavelength of 1 Å. For the OPAA Y212F, the 2.1 Å data set was collected using the SER-CAT beam line 22-BM and a MAR 225 detector. For OPAA Y212F in complex with mipafox and the OPAA FLY, the 2.4 Å data sets were collected using the SER-CAT beam line 22-ID and a MAR300hs detector.

X-ray images were indexed, processed, integrated, and scaled using HKL2000 (Otwinowski, et al., *Macromolecular Crystallography, Part A, Academic Press*, 276 (1997)). An initial phase solution for OPAA Y212F was elucidated using wild-type OPAA [Protein Data Bank (PDB): 3L24] as a starting model for molecular replacement using Phaser (Bailey, *Acta Crystallographica Section D-Biological Crystallography*, 50:760-763 (1994)). Initial structures for the OPAA Y212F with mipafox bound and OPAA FLY were found using the OPAA Y212F structure as a search model.

All structures were subjected to Phenix autobuild in which water molecules were initially added. Subsequent refinement utilized iterative cycles of model building and refinement using COOT and Phenix Refine, respectively (Adams, et al., *Acta Crystallographica Section D-Biological Crystallography*, 66:213-221 (2010); Emsley, et al., *Acta Crystallographica Section D-Biological Crystallography*, 60:2126-2132 (2004)). Water molecules were added and deleted using the check water application in COOT before individually examined. The final model was checked for structural quality using the Molprobity and other Phenix suite validation programs. The data refinement statistics are listed in Table 1.

Results

To grasp how the nature of the active site may have changed by alteration of Tyr212 within the small pocket of the OPAA active site, OPAA Y212F was expressed, purified, and initially screened utilizing crystal conditions from the full-length OPAA (Vyas, et al., *Biochemistry*, 49:547-559 (2010)). Only frail crystals composed of thin plates were obtained after several rounds of optimization. As a result, OPAA Y212F was screened against several suites of commercially available precipitant screens followed by optimization via an additive screen. The final crystal condition was comprised of 4% PEG 4,000 and 20% Isopropanol and was optimized with 0.1 M BaCl2, yielding a 2.1 Å data set in a C2 space group (Table 2).

TABLE 2

Crystallization Data

| # | OPAA Y212 | OPAA Y212 Mipafox | OPAA FLY |
|---|---|---|---|
| Data Collection | | | |
| Space Group | C2 | C2 | C2 |
| Unit Cell Dimensions | | | |
| a, b, c (Å) | 103.4, 67.9, 140.5 | 104.5, 68.2, 142.5 | 102.9 68.8 139.4 |
| α, β, γ (°) | 90.0, 110.1, 90.0 | 90.0, 110.5, 90.0 | 90, 109.6, 90 |
| Resolution (Å) | 50.0-2.1 | 50.0-2.4 | 50.0-2.2 |
| No. Reflections Observed | 182,172 | 124,112 | 209,219 |
| No. Unique Reflections | 49,830 | 37,080 | 46,682 |
| $R_{merge}$ (%)$^a$ | 7.5 (16.1)* | 9.2 (44.2)* | 8.3 (28.4)* |
| I/σI | 18.8 (11.0)* | 10.7 (2.3)* | 18.3 (3.1)* |
| % Completeness | 99.6 (99.9)* | 98.5 (99.2)* | 98.7 (82.8) |
| Refinement | | | |
| Resolution Range | 32.9-2.11 | 48.9-2.4 | 48.5-2.2 |
| No. Reflections in Working Set | 49,820 | 35,090 | 46,673 |
| No. Reflections in Test Set | 2,526 | 1,990 | 2,355 |
| $R_{work}$ (%)$^b$ | 17.2 (19.9)* | 17.6 (22.5)* | 16.2 (21.4)* |
| $R_{free}$ (%)$^b$ | 21.2 (19.0)* | 22.6 (28.8)* | 21.8 (27.8)* |
| RMS deviation: | | | |
| Bond Lengths (Å) | 0.003 | 0.010 | 0.002 |
| Bond Angles (°) | 0.6 | 0.96 | 0.63 |
| Protein/Water/Ligands Atoms | 7,002/712/23 | 6,915/377/38 | 7064/470/19 |

TABLE 2-continued

Crystallization Data

| # | OPAA Y212 | OPAA Y212 Mipafox | OPAA FLY |
|---|---|---|---|
| Average B-Factors (Å$^2$) | | | |
| Total | 29.8 | 39.2 | 45.3 |
| Protein | 29.1 | 39 | 45.1 |
| Water | 36.7 | 40.3 | 48.7 |
| Ligands | 33.8 | 60.1 | 69.1 |

*The last resolution shell is shown in parentheses.
$^a$R$_{merge}$ = $\Sigma_h\Sigma_i$|I$_i$(h) − <I(h)>|/$\Sigma_h\Sigma_i$ I$_i$(h), where I$_i$(h) is the i$^{th}$ measurement and <I(h)> is the weighted mean of all measurements of I(h).
$^b$R$_{work}$ and R$_{free}$ = h(|F(h)$_{obs}$| − |F(h)$_{calc}$|)/h|F(h)$_{obs}$| for reflections in the working and test sets, respectively.
R.M.S., root mean square.

Inspection of the OPAA Y212F active site found organization of the binuclear manganese (II) active site largely and surprisingly unchanged previous from the OPAA structure entry 3L24. The substitution of OPAA Tyr212 with phenylalanine did remove the presence of a hydroxyl group, which formed the underpinning of an H-bonding network between the Tyr212, Asp255, and Asp244 as well as with the amides of Gly246 and Ala245 within wild-type OPAA. Although the dynamics of the active site may have been altered through the loss of this bonding system, the phenylalanine substitution did not appear to drastically impact the binuclear metal organization and coordination within OPAA Y212F. Nor, did the Y212F alteration prevent the observation of additional density beyond the binuclear metal center being visualized within the OPAA Y212F active site. Specifically, considerable Fo-Fc density was observed that could not be accurately fit to any buffer, or crystallographic reagents, including the glycerol, contained in the cryogenic soaking solution. The bulk of this density did appear to match a glycolate that may have been co-purified with the enzyme as previously observed in wild-type OPAA. However, placement of the glycolate still left a significant Fo-Fc peak between the two metals. This signal was only fully accounted for when a hydroxide ion was placed in it. The resulting active site illustrates a mix of first sphere metal bonds ranging from 1.8-2.2 Å and H-Bonds ranging from 2.4-3.5 Å involving the glycolate, hydroxide ion, and coordinating aspartic acid and glutamate residues.

To reveal if any additional alterations may be visualized upon binding a substrate, the pesticide mipafox was co-crystallized with OPAA Y212F under the same conditions as the holo form of OPAA Y212F. Prominent Fo-Fc density was observed within the active site. Refinement with mipafox, or its OPAA facilitated product N,N'-diisopropyl-diamidophosphate (DDP), appeared to indicate the ligand within the active site was DDP. Specifically, the bond distances and geometry formed by its diamidophosphate core within the unaccounted-for density is similar to that found in a wild-type counterpart PDB entry 3L24 and matched the resulting 2Fo-1Fc density (Vyas, et al., *Biochemistry,* 49:547-559 (2010)). This included the diamidophosphate core of DDP forming several first sphere metal bonds with the binuclear metal motif as well as an H-bond to nearby His343. However, the DDP side chains were found to be in distantly different orientations then that of the previous OPAA structure. This may have been the result of the introduction of the Y212F mutation. However, the OPAA residues that would guide the DDP side chain placements within the active site appear relatively unchanged. Even the ring of Phe212 in OPAA Y212F appears to overlay well with that of the tyrosine residue it replaced. This indicates a more likely scenario is that the higher resolution of the OPAA Y212F bound DPP structure (2.4 Å) over that of the wild-type OPAA bound DPP structure (2.7 Å) may have provided greater clarity on their positions. As a result, the position of the DPP side chains in the OPAA Y212 structure may be more representative of their placement within the substrate-binding pocket.

At the monomer level, OPAA Y212F largely mirrors the tertiary and secondary structure of the 440 residues visible in the wild-type OPAA structure (Vyas, et al., *Biochemistry,* 49:547-559 (2010)). Only a few minor differences between secondary structure were noted when the Definition of Secondary Structure of Proteins software (DSSP) was applied to OPAA Y212F. Surprisingly, the large degree of similarity at the secondary and tertiary levels did not extend to the expected quaternary structure. OPAA Y212F was found to be a dimer in the asymmetric unit with electron density being observed for the bulk the 440 amino acids found in the expression construct. Previously, similar wild-type OPAA dimers were proposed within the wild-type OPAA crystal structures I222 lattice. Specifically, asymmetric unit monomers partnering with their lattice mates (Vyas, et al., *Biochemistry,* 49:547-559 (2010); Vyas, et al., *Biochemistry,* 49:2305-2305 (2010)). However, this is where the similarity ends. Previous examination of the wild-type OPAA PDB entries 3L24 and 3L7G within their I222 crystal lattices indicates that wild-type OPAA may form a dimer of dimers (Vyas, et al., *Biochemistry,* 49:547-559 (2010); Vyas, et al., *Biochemistry,* 49:2305-2305 (2010)). However, this type of arrangement is not found in the OPAA Y212F C2 crystal lattice likely ruling out such a quaternary structural organization for at least the OPAA Y212F. Utilizing the Proteins, Interfaces, Structures and Assemblies (PISA) server, the buried surface within the OPAA Y212F dimeric interface is calculated to be 5,910 Å2 and indicates a stable interface. Hence, this indicates that OPAA Y212F is a dimer and the oligomeric structure of its wild-type and closely associate mutations are also likely to be dimeric.

In addition to the lattice differences between OPAA Y212F and its wild-type counterpart, there were some notable differences in missing loops between the two. OPAA Y212F monomers A and B lacked electron density for residues 92-96 and 91-96 respectively, where this loop was observed in the wild-type OPAA structure. However, monomer B of OPAA Y212F was overall more complete than that observed for its monomer A, but also surprisingly for any of the wild-type OPAA monomers. Specifically, electron density was observed for monomer B's residues 348-365. This newly resolved region includes reverse turns not observed in monomer A, or in any of the previously reported three monomers found in the wild-type OPAA structure's asymmetric unit, giving it a handle like appearance (Vyas, et al., *Biochemistry*, 49:547-559 (2010)). Residues 351-354 form a type I reverse turn, where as a type II reverse turn is formed by residues 360-363. Overall, this gives the newly resolved region a handle-like appearance. Lattice packing did not appear to be responsible for visualization of this additional tertiary structure, as this part of the structure is not directly in contact with other monomers, or symmetry mates.

Second round of small pocket optimization further enhances OPAA activity towards VR. Leveraging the improved activities of OPAA containing either the Y212F, or Y212V, mutations, two separate series of mutants were then made respectively in the OPAA Y212F and Y212V backgrounds. In each case, this involved substituting all amino acids at the nearby small pocket-forming Val342 site. Crude lysates from all these mutants were then used to screen for activity on 3 mM VR. None of the Val342 OPAA mutants constructed in the Y212V background showed VR activity increased over the parental Y212V strain; however, several of those from the Y212F background were of interest. In short, the crude lysates of the Y212F/V342C and Y212F/V342I OPAA mutants had specific activities approximately twice that of the Y212F background, the OPAA Y212F/V342W and OPAA Y212F/V342Y lysates were about three times as active as OPAA Y212F and the OPAA Y212F/V342L construct had activity more than seven times that of OPAA Y212F (FIG. 1, Table 1). In short, the mutants V342C, V342W, V342Y and, in particular, V342L all appeared to have VR activity significantly increased over that of the parental Y212F. A closer kinetic examination using purified protein from the top performing OPAA Y212F/V342L mutant against VR, revealed it possessing a $k_{cat}$ for VR that was twice that of Y212F and ten times higher than that of wild-type OPAA. Taking into account OPAA Y212F/V342L's slightly lower KM for VR, OPAA Y212F/V342L boasted five-fold and twenty-fold increased catalytic efficiency over that of OPAA Y212F and wild-type OPAA respectively (Table 1, FIG. 1).

Seeking further improvement in activity, the I215 site proved of interest due to its proximity to the small pocket. Consequently, all amino acids were substituted into the I215 site. Crude lysate specific activity screenings indicated that OPAA Y212F/V342L/I215Y (FLY) was the most active. In-depth analysis revealed its $k_{cat}$ to be twice that of the double mutant OPAA Y212F/V342L, while its $K_M$ towards VR was nearly unchanged (FIG. 1, Table 1). Crude lysate data also indicated that OPAA Y212F/V342L/I215H and OPAA Y212F/V342L/I215F were of interest, but were not as active as the OPAA FLY.

To evaluate the alterations occurring within the OPAA active site due to the triple mutation, the X-ray structure of OPAA FLY was determined to (2.4 Å) using methods similar to those used for the OPAA Y212F structure. Being solved in the same space group and lattice, OPAA FLY at the quaternary, tertiary and secondary structure levels closely resembled the OPAA Y212F structure. Even the additional active site density mirrored the glycolate and the metal bridging hydroxide ion previously observed in the OPAA Y212F structure. Apart from the alterations at of Y212F, V342L, and I215F, only minor differences between the OPAA FLY and other OPAA structures were observed.

Example 3

FLYD Variants have Broader Substrate Specificity

An enzyme's enantiomeric preference, where it exists, can be determined by degrading half the substrate (essentially, the enantiomer on which the activity is greatest) and measuring the direction in which the remaining substrate (i.e., the least preferred enantiomer) rotates plane polarized light in a polarimeter. Following that approach, the PTE enzyme was used to degrade a solution of 1 gram of VR in 1 L of buffer. The reaction was sampled periodically and followed spectrophotometrically and was extracted with ethyl acetate when just over half the starting VR had been degraded. The concentrated ethyl acetate extract of that solution was determined by polarimetry to be comprised predominantly of the P(−) enantiomer, indicating an enzymatic preference for the P(+) enantiomer.

Using knowledge of the enantiomeric preference of one enzyme on one substrate, it is possible to mix that reference enzyme with one of unknown enantiomeric preference at similar activity levels and observe whether their respective preferences are for the same or for different enantiomers of that substrate. If two enzymes prefer the same enantiomer, one enantiomer will not be degraded and the hydrolysis reaction curve will have a midpoint deflection similar to that observed with a single enzyme that strongly prefers one enantiomer. If the two enzymes prefer different enantiomers such that the activity of one enzyme complements the activity of the other, no such midpoint deflection will be observed, resulting in a typical single exponential curve. Using this approach, it was determined that the OPAA WT enzyme possessed the same enantiomeric preference as PTE; i.e., it preferentially catalyzed the P(+) enantiomer.

FIG. 2 shows the patterns of OPAA wild-type, F, FL, and FLY enzymes on 0.18 mM VR. The concentration of VR was selected to allow a complete reaction within the dynamic range of the spectrophotometer. Wild-type enzyme and the F, FL and FLY mutant OPAA enzymes all exhibit an almost absolute specificity for a single enantiomer of VR, as evidenced by the relatively rapid initial rate followed by an abrupt midpoint deflection to a rate approximating that of spontaneous VR hydrolysis (FIG. 2).

Studying the OPAA Y212F active site with mipafox bound as well as the OPAA FLY active site, a search was conducted for residues to be targeted for mutation in order to broaden the stereospecificity of OPAA FLY. Of the ones considered, His343 was of particular interest. It was the lone residue not optimized within the small pocket, and it formed an H-bond with an oxygen atom with the diamidophosphate core potentially orienting the bound ligand. Two mutants were constructed at the His343 site—H343D and H343A. One, H343D, exhibited activity towards both enantiomers of VR. This mutant, designated FLYD, illustrated a relatively constant rate for the entire reaction with a final magnitude twice that of the others, indicative of FLYD having similar activity on both enantiomers of VR. Overall, kinetic analysis of FLYD revealed it possesses a $k_{cat}$ of 18 min-1, while its VR $K_M$ was 2,075 μM on racemic VR, equating to a catalytic efficiency of 8,890 $M^{-1}$ $min^{-1}$, or approximately half that of FLY, although more importantly, the stereospecificity of the FLYD has been dramatically broadened, as compared to previous versions of the enzyme.

CONCLUSIONS

Unlike the amidohydrolase superfamily of phosphotriesterases (PTE) where a number of X-ray structures have been solved and support their proposed catalytic mechanism, structure information on OPAA has been is relatively scarce. Most of the information pertaining to the OPAA catalytic mechanism has been derived from studies of a structurally similar enzyme to OPAA known as aminopeptidase P (AMPP) (Bigley, et al., *Biochimica et Biophysica Acta*, 1834:443-453 (2013); Huang, et al., *Chembiochem: A European Journal of Chemical Biology*, 7:506-514 (2006)). The currently-envisioned mechanism for OPAA is where a substrate enters the substrate-binding site and displaces waters bound to the manganese (II) ions. Subsequently, hydroxide bridging between two manganese (II) ions has been proposed to carry out a nucleophilic attack on the phosphorus center of the substrate in question triggering the formation of an intermediate. This intermediate subsequently collapses with the departure of the leaving group (Bigley, et al., *Biochimica et Biophysica Acta*, 1834:443-453 (2013)). In the only two previous known structures of OPAA, the hydroxide ion at the center of the proposed mechanism has been difficult to fully confirm (Vyas, et al., *Biochemistry*, 49:547-559 (2010)). However, within the OPAA Y212F and FLY structures, clear density is observed for the presence of a hydroxide ion being bridged by the two manganese (II) ions. In an earlier study, an aspartate acid within the PTE family of enzymes was shown to form a hydrogen bond with the hydroxide ion priming it for its role in catalysis (Bigley, et al., *Biochimica et Biophysica Acta*, 1834:443-453 (2013)). The placement of the hydroxide with the OPAA Y212F and FLY structures directly implicates Glu381 to fill this role for OPAAs. In addition to coordinating one of the two manganese (II) ions within the OPAA active site, Glu381 is in a prime location and orientation to form the requisite hydrogen bond.

With the larger side chain moieties of the V-series agents to those of the G-series, an assumption might be that increasing the size of the substrate-binding site would facilitate greater OPAA activity towards the larger organophosphates such as the V-series agents including VR. However, it is not that straightforward. In actuality, the mutational screening data indicates that the plasticity within of certain parts of the small pocket and its shape are the predominate influences for increased activity towards VR.

For instance at the Y212 site, substitutions that would likely have disrupted a hydrogen bonding network tying the upper part of the small pocket to manganese (II) coordinating Asp255 seemed to be favored. In general, residues at this location that likely would not hamper hydrophobic interactions, or create steric clashes with nearby Val342 also appear to be better substitutes. The mutational data for the 342 site appears to attest to desirable nature of a hydrophobic connection between the 342 and 212 sites for heightened OPAA VR capability. Specifically, the substitution of leucine at the 342 site appears to balance increasing hydrophobic interactions with the substituted phenylalanine at position 212 without creating steric clashes. Put together, the stronger hydrophobic interactions along the wall of the small pocket, while increasing the plasticity of the wall relative to the manganese (II) active site core appears to be beneficial for VR catalysis.

However, the additional plasticity resulting from the Y212F mutation may not be the only factor in the increased rate of catalysis of the Y212F OPAA mutant. The presence of the hydroxide ion within the structures of the Y212F and FLY OPAAs and not in the wild-type OPAA might offer an additional clue. Specifically, the loss of the H-bonds formed by the replacement of tyrosine with phenylalanine at position 212 alters the H-bonding network in a manner that allows for more stable interactions between the active site hydroxide ion and neighboring residues. One possible candidate would be D244. Whereas D244 forms H-bonds with Y212 in wild-type OPAA, these interactions are no longer available for D244 in Y212F OPAA and subsequent Y212F mutation-containing mutants. This could translate into D244 being more available to facilitate interactions with the observed active site hydroxide ion that is only 2.8 Å away and stabilize its presence. This stabilizing effect on the hydroxide ion by D244 or other active site residues as a result of the Y212F mutation-containing OPAA mutants could in turn heighten catalytic activity within the proposed enzymatic mechanism (Bigley, et al., *Biochim. Biophys. Acta, Proteins Proteomics*, 1834, 443-453 (2013)).

In addition to these factors and contrary to initial assumptions, shrinking the small pocket appears to also be beneficial for catalysis of VR. As the screening data illustrates, significant relative increases in activity towards VR was found when an Ile215 was exchanged with residues possessing bulkier side chains. These substitutes narrow the size of the small pocket significantly. With little unchanged outside of the sites that were mutated within the OPAA substrate binding site and accompanying manganese (II) ion core, the narrowing of the active site appears to indicate that the narrow small pocket could restrict VR to an orientation more favorable for catalysis. Understandably, without a structure of VR within the OPAA FLY active site, determining the exact effect on VR positioning by the narrowing of the small pocket for the increase of OPAA catalytic activity towards VR as a result of the narrowing of the small pocket is difficult. However, small changes in orientation of enzymatic substrates due to mutations away from the active site has been observed to result in large catalytic differences and this may be the case for OPAA and VR (Mesecar, et al., *Science*, 277:202-206 (1997)).

With differing levels of toxicity known between enantiomers of organophosphates, enzymes that can process either the more toxic enantiomer, or both of a given organophosphate would be preferred. Using the DPP bound OPAA Tyr212 and wild-type structures as a guide; three points of contact within the substrate-binding site were believed to contribute to OPAA's substrate stereospecificity. Two are based in favorable interactions between the DPP side chains and the small and large pockets. One other could be located with interactions with DPP's diamidophosphate core and enzyme's binuclear metal core.

Beyond these points of contact, a fourth is likely present in the form of a H-bond between the Nε2 of the His343 side chain and an oxygen atom from the diamidophosphate core. In recent reports, His343 has been identified to assist in polarization of scissile peptide carbonyl bonds within naturally occurring peptide substrates (Vyas, et al., *Biochemistry*, 49:547-559 (2010)). In regards to organophosphates, the previously proposed catalytic mechanism indicated His343 could assist in positioning them for catalysis (Bigley, et al., *Biochimica et Biophysica Acta*, 1834:443-453 (2013)). Although this seems straightforward for the binding and catalysis of several organophosphate classes including V-series agents for their respective P(+)enantiomers, the bulky side chain of His343 might sterically hinder P(−)enantiomers from accessing the active site in a catalytically viable manner. As a result, the broadened activity observed at the expense of some catalytic efficiency in the OPAA FLYD mutant could be due to the removal of the steric hindrance H343 poses towards P(−)enantiomers. Naturally, this alteration of His343 may dampen some catalytic activity of one enantiomer over another. However, the broader substrate activity overall is quite a boon for considering OPAA for the role of catalytic antidote. Combined with the high levels of expression, stability and high GD activity of this enzyme, the OPAA FLY and FLYD mutants also appear to offer potentially suitable platforms for further modifications aimed at increasing the catalytic efficiency of this enzyme on VR.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A genetically engineered organophosphorous acid anhydrolase (OPAA) polypeptide, wherein the genetically engineered OPPA polypeptide has broadened substrate specificity relative to the OPPA polypeptide of SEQ ID NO:5 by replacing at least one basic amino acid within the small pocket of the OPAA with an acidic amino acid or its amide,
    wherein the OPPA comprises an amino acid sequence at least 90% identical to the region from amino acid residue 212 to residue 343 of SEQ ID NO:12, and
    wherein the amino acid at the residue corresponding to residue 343 of SEQ ID NO:12 is not a histidine.

2. The genetically engineered OPAA polypeptide of claim 1, wherein the OPPA comprises the amino acid sequence of the region from amino acid residue 212 to residue 343 of SEQ ID NO:12, and wherein the amino acid at the residue corresponding to residue 343 of SEQ ID NO:12 is not a histidine.

3. The genetically engineered OPAA polypeptide of claim 1, wherein the OPAA comprises the amino acid sequence of the region from amino acid residue 212 to residue 343 of SEQ ID NO:6, 14, or 15.

4. The genetically engineered OPAA polypeptide of claim 1, wherein the OPAA comprises the amino acid sequence of the region from amino acid residue 212 to residue 343 of SEQ ID NO:7.

5. The genetically engineered OPAA polypeptide of claim 1, wherein the OPAA comprises the amino acid sequence of SEQ ID NO:12, with or without the N-terminal methionine.

6. The genetically engineered OPAA polypeptide of claim 1, wherein the OPAA comprises the amino acid sequence of SEQ ID NO:6, 14, or 15 with or without the N-terminal methionine.

7. The genetically engineered OPAA polypeptide of claim 1, wherein the OPAA comprises the amino acid sequence of SEQ ID NO:7, with or without the N-terminal methionine.

8. The genetically engineered OPAA polypeptide of claim 1, wherein the OPAA has catalytic activity for both enantiomers of a V-type nerve agent; has increased OPAA activity towards the Sp/ P(−) enantiomer of a V-type nerve agent; or the combination thereof relative to the OPAA polypeptide of SEQ ID NO:5.

9. The genetically engineered OPAA polypeptide of claim 8, wherein the V-type nerve agent is VR or VX.

10. A method of treating or inhibiting organophosphate exposure or poisoning in a subject comprising administering the subject an effective amount the engineered OPAA of claim 1 to reduce the level or activity of the organophosphate.

11. The method of claim 8, wherein the subject was exposed to or is at risk of being exposed to a V-type nerve agent.

12. The method of claim 11, wherein the V-type nerve agent is VX or VR.

13. The method of claim 10, wherein the subject has one or more symptoms of organophosphorus exposure.

14. The method of claim 13, wherein the one or more symptoms comprise peripheral or central nervous system damage, myopathy, psychosis, general paralysis, twitching, trembling, paralyzed breathing, convulsions, miosis, blurred vision, dark vision, headache, nausea, dizziness, vomiting, hypersecretion, sweating, salivation, lacrimation, rhinorrhea, abdominal cramps, diarrhea, urinary incontinence, muscle twitching/fasciculations, paralysis, pallor, muscle weakness, tremors, convulsions, incoordination, diaphoresis, bronchospasm, bronchorrhea, tightness in chest, wheezing, productive cough, pulmonary edema, bradycardia, sinus arrest, tachycardia, hypertension, toxic myocardiopathy, mydriasis, ataxia, anxiety, restlessness, choreiform movement, loss of consciousness, respiratory depression, fatigue, seizures, depression, memory loss, confusion, or a combination thereof.

15. The method of claim 10, further comprising administering the subject atropine, 2-PAM, a benzodiazepine, or a combination thereof.

16. The method of claim 10, wherein the OPAA is administered in an effective amount to reduce the LD50 of the organophosphate.

17. The method of claim 10, wherein the OPAA is present in a pharmaceutical composition that is administered into the bloodstream of the subject via injection, infusion, pulmonary administration, or intranasal administration.

18. A method of decontaminating a surface or liquid exposed to an organophosphate comprising contacting the surface or liquid with an effective amount of the OPAA of claim 1 to reduce the level or activity of the agent.

19. The method of claim 18, wherein the OPAA is a liquid, powder, or foam formulation.

20. An organophosphorous acid anhydrolase (OPAA) comprising an amino acid sequence at least 85% identical to SEQ ID NO:14,
    wherein the amino acid residue corresponding to residue 343 of SEQ ID NO:14 is asparagine (N), aspartic acid (D), glutamine (Q), or glutamic acid (E).

21. The OPAA of claim 20, wherein amino acid residue corresponding to residue 212 is phenylalanine (F).

22. The OPAA of claim 21, wherein amino acid residue corresponding to residue 342 is lysine (L).

23. The OPAA of claim 22, wherein amino acid residue corresponding to residue 215 is tyrosine (Y).

24. The OPAA of claim 20, comprising the amino acid sequence of SEQ ID NO:7.

\* \* \* \* \*

SEQUENCE LISTING

<160> NUMBER OF SEQ ID NOS: 15

<210> SEQ ID NO 1
<211> LENGTH: 517
<212> TYPE: PRT
<213> ORGANISM: Alteromonas sp. JD6.5

<400> SEQUENCE: 1

Met Asn Lys Leu Ala Val Leu Tyr Ala Glu His Ile Ala Thr Leu Gln
1 5 10 15

Lys Arg Thr Arg Glu Ile Ile Glu Arg Glu Asn Leu Asp Gly Val Val
20 25 30

Phe His Ser Gly Gln Ala Lys Arg Gln Phe Leu Asp Asp Met Tyr Tyr
35 40 45

Pro Phe Lys Val Asn Pro Gln Phe Lys Ala Trp Leu Pro Val Ile Asp
50 55 60

Asn Pro His Cys Trp Ile Val Ala Asn Gly Thr Asp Lys Pro Lys Leu
65 70 75 80

Ile Phe Tyr Arg Pro Val Asp Phe Trp His Lys Val Pro Asp Glu Pro
85 90 95

Asn Glu Tyr Trp Ala Asp Tyr Phe Asp Ile Glu Leu Leu Val Lys Pro
100 105 110

Asp Gln Val Glu Lys Leu Leu Pro Tyr Asp Lys Ala Arg Phe Ala Tyr
115 120 125

Ile Gly Glu Tyr Leu Glu Val Ala Gln Ala Leu Gly Phe Glu Leu Met
130 135 140

Asn Pro Glu Pro Val Met Asn Phe Tyr His Tyr His Arg Ala Tyr Lys
145 150 155 160

Thr Gln Tyr Glu Leu Ala Cys Met Arg Glu Ala Asn Lys Ile Ala Val
165 170 175

Gln Gly His Lys Ala Ala Arg Asp Ala Phe Phe Gln Gly Lys Ser Glu
180 185 190

Phe Glu Ile Gln Gln Ala Tyr Leu Leu Ala Thr Gln His Ser Glu Asn
195 200 205

Asp Asn Ala Tyr Gly Asn Ile Val Ala Leu Asn Glu Asn Cys Ala Ile
210 215 220

Leu His Tyr Thr His Phe Asp Arg Val Ala Pro Ala Thr His Arg Ser
225 230 235 240

Phe Leu Ile Asp Ala Gly Ala Asn Phe Asn Gly Tyr Ala Ala Asp Ile
245 250 255

Thr Arg Thr Tyr Asp Phe Thr Gly Glu Gly Glu Phe Ala Glu Leu Val
260 265 270

Ala Thr Met Lys Gln His Gln Ile Ala Leu Cys Asn Gln Leu Ala Pro
275 280 285

Gly Lys Leu Tyr Gly Glu Leu His Leu Asp Cys His Gln Arg Val Ala
290 295 300

```
Gln Thr Leu Ser Asp Phe Asn Ile Val Asp Leu Ser Ala Asp Glu Ile
305                 310                 315                 320

Val Ala Lys Gly Ile Thr Ser Thr Phe Phe Pro His Gly Leu Gly His
            325                 330                 335

His Ile Gly Leu Gln Val His Asp Val Gly Gly Phe Met Ala Asp Glu
        340                 345                 350

Gln Gly Ala His Gln Glu Pro Pro Glu Gly His Pro Phe Leu Arg Cys
    355                 360                 365

Thr Arg Lys Ile Glu Ala Asn Gln Val Phe Thr Ile Glu Pro Gly Leu
370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
            405                 410                 415

Ile Arg Ile Glu Asp Asn Ile Ile Val His Glu Asp Ser Leu Glu Asn
        420                 425                 430

Met Thr Arg Glu Leu Arg Ala Arg Leu Thr Thr His Ser Leu Arg Gly
    435                 440                 445

Leu Ser Ala Pro Gln Phe Ser Ile Asn Asp Pro Ala Val Met Ser Glu
450                 455                 460

Tyr Ser Tyr Pro Ser Glu Pro Leu Ser Tyr Glu Glu Ile Lys Lys
465                 470                 475                 480

Ser Thr Phe Ile Val His Val Arg Thr Arg Ile Leu Val Arg Arg
            485                 490                 495

Arg Thr Leu Ser Pro Ile Leu Ile Ala Val Thr Pro Met Pro Ala Ile
            500                 505                 510

Thr Ala Gly Leu Met
        515

<210> SEQ ID NO 2
<211> LENGTH: 517
<212> TYPE: PRT
<213> ORGANISM: Artificial Sequence
<220> FEATURE:
<223> OTHER INFORMATION: Synthetic Polypeptide - Organophosphate acid
      anhydrolase

<400> SEQUENCE: 2

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140
```

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
            165                 170                 175

Gln Gly His Lys Ala Ala Arg Asp Ala Phe Phe Gln Gly Lys Ser Glu
        180                 185                 190

Phe Glu Ile Gln Gln Ala Tyr Leu Leu Ala Thr Gln His Ser Glu Asn
    195                 200                 205

Asp Thr Pro Tyr Gly Asn Ile Val Ala Leu Asn Glu Asn Cys Ala Ile
210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
            245                 250                 255

Thr Arg Thr Tyr Asp Phe Thr Gly Glu Gly Glu Phe Ala Glu Leu Val
        260                 265                 270

Ala Thr Met Lys Gln His Gln Ile Ala Leu Cys Asn Gln Leu Ala Pro
    275                 280                 285

Gly Lys Leu Tyr Gly Glu Leu His Leu Asp Cys His Gln Arg Val Ala
290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
            325                 330                 335

His Ile Gly Leu Gln Val His Asp Val Gly Phe Met Ala Asp Glu
        340                 345                 350

Gln Gly Ala His Gln Glu Pro Pro Glu Gly His Pro Phe Leu Arg Cys
    355                 360                 365

Thr Arg Lys Ile Glu Ala Asn Gln Val Phe Thr Ile Glu Pro Gly Leu
370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
            405                 410                 415

Ile Arg Ile Glu Asp Asn Ile Ile Val His Glu Asp Ser Leu Glu Asn
        420                 425                 430

Met Thr Arg Glu Leu Arg Ala Arg Leu Thr Thr His Ser Leu Arg Gly
    435                 440                 445

Leu Ser Ala Pro Gln Phe Ser Ile Asn Asp Pro Ala Val Met Ser Glu
450                 455                 460

Tyr Ser Tyr Pro Ser Glu Pro Leu Ser Tyr Glu Glu Ile Lys Lys
465                 470                 475                 480

Ser Thr Phe Ile Val His Val Arg Thr Arg Arg Ile Leu Val Arg Arg
            485                 490                 495

Arg Thr Leu Ser Pro Ile Leu Ile Ala Val Thr Pro Met Pro Ala Ile
        500                 505                 510

Thr Ala Gly Leu Met
        515

<210> SEQ ID NO 3
<211> LENGTH: 440
<212> TYPE: PRT
<213> ORGANISM: Artificial Sequence
<220> FEATURE:

<223> OTHER INFORMATION: Synthetic Polypeptide - Fragment of SEQ ID NO:1

<400> SEQUENCE: 3

| | | | | | | | | | | | | | | |
|---|---|---|---|---|---|---|---|---|---|---|---|---|---|---|
| Met | Asn | Lys | Leu | Ala | Val | Leu | Tyr | Ala | Glu | His | Ile | Ala | Thr | Leu | Gln |
| 1 | | | | 5 | | | | | 10 | | | | | 15 | |
| Lys | Arg | Thr | Arg | Glu | Ile | Ile | Glu | Arg | Glu | Asn | Leu | Asp | Gly | Val | Val |
| | | | 20 | | | | | 25 | | | | | 30 | | |
| Phe | His | Ser | Gly | Gln | Ala | Lys | Arg | Gln | Phe | Leu | Asp | Asp | Met | Tyr | Tyr |
| | | 35 | | | | | 40 | | | | | 45 | | | |
| Pro | Phe | Lys | Val | Asn | Pro | Gln | Phe | Lys | Ala | Trp | Leu | Pro | Val | Ile | Asp |
| | 50 | | | | | 55 | | | | | 60 | | | | |
| Asn | Pro | His | Cys | Trp | Ile | Val | Ala | Asn | Gly | Thr | Asp | Lys | Pro | Lys | Leu |
| 65 | | | | | 70 | | | | | 75 | | | | | 80 |
| Ile | Phe | Tyr | Arg | Pro | Val | Asp | Phe | Trp | His | Lys | Val | Pro | Asp | Glu | Pro |
| | | | | 85 | | | | | 90 | | | | | 95 | |
| Asn | Glu | Tyr | Trp | Ala | Asp | Tyr | Phe | Asp | Ile | Glu | Leu | Leu | Val | Lys | Pro |
| | | | 100 | | | | | 105 | | | | | 110 | | |
| Asp | Gln | Val | Glu | Lys | Leu | Leu | Pro | Tyr | Asp | Lys | Ala | Arg | Phe | Ala | Tyr |
| | | 115 | | | | | 120 | | | | | 125 | | | |
| Ile | Gly | Glu | Tyr | Leu | Glu | Val | Ala | Gln | Ala | Leu | Gly | Phe | Glu | Leu | Met |
| | 130 | | | | | 135 | | | | | 140 | | | | |
| Asn | Pro | Glu | Pro | Val | Met | Asn | Phe | Tyr | His | Tyr | His | Arg | Ala | Tyr | Lys |
| 145 | | | | | 150 | | | | | 155 | | | | | 160 |
| Thr | Gln | Tyr | Glu | Leu | Ala | Cys | Met | Arg | Glu | Ala | Asn | Lys | Ile | Ala | Val |
| | | | | 165 | | | | | 170 | | | | | 175 | |
| Gln | Gly | His | Lys | Ala | Ala | Arg | Asp | Ala | Phe | Phe | Gln | Gly | Lys | Ser | Glu |
| | | | 180 | | | | | 185 | | | | | 190 | | |
| Phe | Glu | Ile | Gln | Gln | Ala | Tyr | Leu | Leu | Ala | Thr | Gln | His | Ser | Glu | Asn |
| | | 195 | | | | | 200 | | | | | 205 | | | |
| Asp | Asn | Ala | Tyr | Gly | Asn | Ile | Val | Ala | Leu | Asn | Glu | Asn | Cys | Ala | Ile |
| | 210 | | | | | 215 | | | | | 220 | | | | |
| Leu | His | Tyr | Thr | His | Phe | Asp | Arg | Val | Ala | Pro | Ala | Thr | His | Arg | Ser |
| 225 | | | | | 230 | | | | | 235 | | | | | 240 |
| Phe | Leu | Ile | Asp | Ala | Gly | Ala | Asn | Phe | Asn | Gly | Tyr | Ala | Ala | Asp | Ile |
| | | | | 245 | | | | | 250 | | | | | 255 | |
| Thr | Arg | Thr | Tyr | Asp | Phe | Thr | Gly | Glu | Gly | Glu | Phe | Ala | Glu | Leu | Val |
| | | | 260 | | | | | 265 | | | | | 270 | | |
| Ala | Thr | Met | Lys | Gln | His | Gln | Ile | Ala | Leu | Cys | Asn | Gln | Leu | Ala | Pro |
| | | 275 | | | | | 280 | | | | | 285 | | | |
| Gly | Lys | Leu | Tyr | Gly | Glu | Leu | His | Leu | Asp | Cys | His | Gln | Arg | Val | Ala |
| | 290 | | | | | 295 | | | | | 300 | | | | |
| Gln | Thr | Leu | Ser | Asp | Phe | Asn | Ile | Val | Asp | Leu | Ser | Ala | Asp | Glu | Ile |
| 305 | | | | | 310 | | | | | 315 | | | | | 320 |
| Val | Ala | Lys | Gly | Ile | Thr | Ser | Thr | Phe | Phe | Pro | His | Gly | Leu | Gly | His |
| | | | | 325 | | | | | 330 | | | | | 335 | |
| His | Ile | Gly | Leu | Gln | Val | His | Asp | Val | Gly | Gly | Phe | Met | Ala | Asp | Glu |
| | | | 340 | | | | | 345 | | | | | 350 | | |
| Gln | Gly | Ala | His | Gln | Glu | Pro | Pro | Glu | Gly | His | Pro | Phe | Leu | Arg | Cys |
| | | 355 | | | | | 360 | | | | | 365 | | | |
| Thr | Arg | Lys | Ile | Glu | Ala | Asn | Gln | Val | Phe | Thr | Ile | Glu | Pro | Gly | Leu |
| | 370 | | | | | 375 | | | | | 380 | | | | |
| Tyr | Phe | Ile | Asp | Ser | Leu | Leu | Gly | Asp | Leu | Ala | Ala | Thr | Asp | Asn | Asn |
| 385 | | | | | 390 | | | | | 395 | | | | | 400 |

```
Gln His Ile Asn Trp Asp Lys Val Ala Glu Leu Lys Pro Phe Gly Gly
            405                 410                 415
Ile Arg Ile Glu Asp Asn Ile Ile Val His Glu Asp Ser Leu Glu Asn
        420                 425                 430
Met Thr Arg Glu Leu Arg Ala Arg
        435                 440

<210> SEQ ID NO 4
<211> LENGTH: 440
<212> TYPE: PRT
<213> ORGANISM: Artificial Sequence
<220> FEATURE:
<223> OTHER INFORMATION: Synthetic Polypeptide - Fragment of SEQ ID NO:2

<400> SEQUENCE: 4

Met Asn Lys Leu Ala Val Leu Tyr Ala Glu His Ile Ala Thr Leu Gln
1               5                   10                  15
Lys Arg Thr Arg Glu Ile Ile Glu Arg Glu Asn Leu Asp Gly Val Val
            20                  25                  30
Phe His Ser Gly Gln Ala Lys Arg Gln Phe Leu Asp Asp Met Tyr Tyr
        35                  40                  45
Pro Phe Lys Val Asn Pro Gln Phe Lys Ala Trp Leu Pro Val Ile Asp
    50                  55                  60
Asn Pro His Cys Trp Ile Val Ala Asn Gly Thr Asp Lys Pro Lys Leu
65                  70                  75                  80
Ile Phe Tyr Arg Pro Val Asp Phe Trp His Lys Val Pro Asp Glu Pro
                85                  90                  95
Asn Glu Tyr Trp Ala Asp Tyr Phe Asp Ile Glu Leu Leu Val Lys Pro
            100                 105                 110
Asp Gln Val Glu Lys Leu Leu Pro Tyr Asp Lys Ala Arg Phe Ala Tyr
        115                 120                 125
Ile Gly Glu Tyr Leu Glu Val Ala Gln Ala Leu Gly Phe Glu Leu Met
    130                 135                 140
Asn Pro Glu Pro Val Met Asn Phe Tyr His Tyr His Arg Ala Tyr Lys
145                 150                 155                 160
Thr Gln Tyr Glu Leu Ala Cys Met Arg Glu Ala Asn Lys Ile Ala Val
                165                 170                 175
Gln Gly His Lys Ala Ala Arg Asp Ala Phe Phe Gln Gly Lys Ser Glu
            180                 185                 190
Phe Glu Ile Gln Gln Ala Tyr Leu Leu Ala Thr Gln His Ser Glu Asn
        195                 200                 205
Asp Thr Pro Tyr Gly Asn Ile Val Ala Leu Asn Glu Asn Cys Ala Ile
    210                 215                 220
Leu His Tyr Thr His Phe Asp Arg Val Ala Pro Ala Thr His Arg Ser
225                 230                 235                 240
Phe Leu Ile Asp Ala Gly Ala Asn Phe Asn Gly Tyr Ala Ala Asp Ile
                245                 250                 255
Thr Arg Thr Tyr Asp Phe Thr Gly Glu Gly Glu Phe Ala Glu Leu Val
            260                 265                 270
Ala Thr Met Lys Gln His Gln Ile Ala Leu Cys Asn Gln Leu Ala Pro
        275                 280                 285
Gly Lys Leu Tyr Gly Glu Leu His Leu Asp Cys His Gln Arg Val Ala
    290                 295                 300
Gln Thr Leu Ser Asp Phe Asn Ile Val Asn Leu Ser Ala Asp Glu Ile
305                 310                 315                 320
```

```
Val Ala Lys Gly Ile Thr Ser Thr Phe Phe Pro His Gly Leu Gly His
            325                 330                 335

His Ile Gly Leu Gln Val His Asp Val Gly Gly Phe Met Ala Asp Glu
        340                 345                 350

Gln Gly Ala His Gln Glu Pro Pro Glu Gly His Pro Phe Leu Arg Cys
            355                 360                 365

Thr Arg Lys Ile Glu Ala Asn Gln Val Phe Thr Ile Glu Pro Gly Leu
        370                 375                 380

Tyr Phe Ile Asp Ser Leu Leu Gly Asp Leu Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Arg Ala Arg
        435                 440

<210> SEQ ID NO 5
<211> LENGTH: 440
<212> TYPE: PRT
<213> ORGANISM: Artificial Sequence
<220> FEATURE:
<223> OTHER INFORMATION: Synthetic Polypeptide - Organophosphate acid
      anhydrolase

<400> SEQUENCE: 5

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Tyr Gly Asn Ile Val Ala Leu Asn Glu Asn Cys Ala Ile
    210                 215                 220

Leu His Tyr Thr His Phe Asp Arg Val Ala Pro Ala Thr His Arg Ser
225                 230                 235                 240
```

```
Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Val His Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
    370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Glu Leu Asp
        435                 440

<210> SEQ ID NO 6
<211> LENGTH: 440
<212> TYPE: PRT
<213> ORGANISM: Artificial Sequence
<220> FEATURE:
<223> OTHER INFORMATION: Synthetic Polypeptide - Organophosphate acid
      anhydrolase
<220> FEATURE:
<221> NAME/KEY: MISC_FEATURE
<222> LOCATION: (212)..(212)
<223> OTHER INFORMATION: Xaa can be tyrosine (Y), valine (V), glycine
      (G), phenylalanine (F), proline (P), glutamine (Q), or threonine
      (T).
<220> FEATURE:
<221> NAME/KEY: MISC_FEATURE
<222> LOCATION: (215)..(215)
<223> OTHER INFORMATION: Xaa can be isoleusine (I), tyrosine (Y),
      histidine (H), or phenylalanine (F).
<220> FEATURE:
<221> NAME/KEY: MISC_FEATURE
<222> LOCATION: (342)..(342)
<223> OTHER INFORMATION: Xaa can be valine (V), cysteine (C),
      isoleusine (I), tryptophan (W), tyrosine (Y), or lysine (L).

<400> SEQUENCE: 6

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60
```

Asn Pro His Cys Trp Ile Val Ala Asn Gly Thr Asp Lys Pro Lys Leu
 65                  70                  75                  80

Ile Phe Tyr Arg Pro Val Asp Phe Trp His Lys Val Pro Asp Glu Pro
                 85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Xaa Gly Asn Xaa Val Ala Leu Asn Glu Asn Cys Ala Ile
210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Xaa Asp Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Glu Leu Asp
        435                 440

<210> SEQ ID NO 7
<211> LENGTH: 440
<212> TYPE: PRT
<213> ORGANISM: Artificial Sequence
<220> FEATURE:
<223> OTHER INFORMATION: Artifical Polypeptide - Organophosphate acid anhydrolase - "FLYD"

<400> SEQUENCE: 7

```
Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Phe Gly Asn Tyr Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Leu Asp Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
    370                 375                 380

Tyr Phe Ile Asp Ser Leu Leu Gly Asp Leu Ala Ala Thr Asp Asn Asn
385                 390                 395                 400
```

-continued

Gln His Ile Asn Trp Asp Lys Val Ala Glu Leu Lys Pro Phe Gly Gly
            405                 410                 415

Ile Arg Ile Glu Asp Asn Ile Ile Val His Glu Asp Ser Leu Glu Asn
        420                 425                 430

Met Thr Arg Glu Leu Glu Leu Asp
        435                 440

<210> SEQ ID NO 8
<211> LENGTH: 8
<212> TYPE: PRT
<213> ORGANISM: Artificial Sequence
<220> FEATURE:
<223> OTHER INFORMATION: Synthetic Polypeptide - FLAG tag

<400> SEQUENCE: 8

Asp Tyr Lys Asp Asp Asp Asp Lys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide - haemagglutinin (HA) tag

<400> SEQUENCE: 9

Tyr Pro Tyr Asp Val Pro
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide -  MYC tag

<400> SEQUENCE: 10

Ile Leu Lys Lys Ala Thr Ala Tyr Ile Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Polypeptide - MYC tag

<400> SEQUENCE: 11

Glu Gln Lys Leu Ile Ser Glu Glu Asp Leu
1               5                   10

<210> SEQ ID NO 12
<211> LENGTH: 440
<212> TYPE: PRT
<213> ORGANISM: Artificial Sequence
<220> FEATURE:
<223> OTHER INFORMATION: Synthetic Polypeptide - Organophosphate acid
      anhydrolase
<220> FEATURE:
<221> NAME/KEY: MISC_FEATURE
<222> LOCATION: (212)..(212)
<223> OTHER INFORMATION: Xaa can be tyrosine (Y), valine (V), glycine
      (G), phenylalanine (F), proline (P), glutamine (Q), or threonine
      (T).
<220> FEATURE:
<221> NAME/KEY: MISC_FEATURE
<222> LOCATION: (215)..(215)
<223> OTHER INFORMATION: Xaa can be isoleusine (I), tyrosine (Y), histidine (H), or phenylalanine (F).
<220> FEATURE:
<221> NAME/KEY: MISC_FEATURE
<222> LOCATION: (342)..(342)
<223> OTHER INFORMATION: Xaa can be valine (V), cysteine (C),
    isoleusine (I), tryptophan (W), tyrosine (Y), or lysine (L).
<220> FEATURE:
<221> NAME/KEY: MISC_FEATURE
<222> LOCATION: (343)..(343)
<223> OTHER INFORMATION: Xaa can be ala (A), arg (R), asn (N), asp (D),
    cys (C), gln (Q), glu (E), gly (G), ile (I), leu (L), lys (K),
    met (M), phe (F), pro (P), ser (S), thr (T), tryp (W), tyr (Y),
    or val (V).

<400> SEQUENCE: 12

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Xaa Gly Asn Xaa Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

```
His Ile Gly Leu Gln Xaa Xaa Asp Val Gly Phe Met Ala Asp Glu
            340             345                 350

Gln Gly Ala His Gln Glu Pro Pro Glu Gly His Pro Phe Leu Arg Cys
            355                 360                 365

Thr Arg Lys Ile Glu Ala Asn Gln Val Phe Thr Ile Glu Pro Gly Leu
        370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Glu Leu Asp
            435                 440

<210> SEQ ID NO 13
<211> LENGTH: 440
<212> TYPE: PRT
<213> ORGANISM: Artificial Sequence
<220> FEATURE:
<223> OTHER INFORMATION: Synthetic Polypeptide - Organophosphate acid
      anhydrolase - "FLY"

<400> SEQUENCE: 13

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Phe Gly Asn Tyr Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255
```

```
Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Leu His Asp Val Gly Gly Phe Met Ala Asp Glu
            340                 345                 350

Gln Gly Ala His Gln Glu Pro Pro Glu Gly His Pro Phe Leu Arg Cys
        355                 360                 365

Thr Arg Lys Ile Glu Ala Asn Gln Val Phe Thr Ile Glu Pro Gly Leu
    370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Glu Leu Asp
        435                 440

<210> SEQ ID NO 14
<211> LENGTH: 440
<212> TYPE: PRT
<213> ORGANISM: Artificial Sequence
<220> FEATURE:
<223> OTHER INFORMATION: Synthetic Polypeptide - Organophosphate acid
      anhydrolase
<220> FEATURE:
<221> NAME/KEY: MISC_FEATURE
<222> LOCATION: (212)..(212)
<223> OTHER INFORMATION: Xaa can be tyrosine (Y), valine (V), glycine
      (G), phenylalanine (F), proline (P), glutamine (Q), or threonine
      (T).
<220> FEATURE:
<221> NAME/KEY: MISC_FEATURE
<222> LOCATION: (215)..(215)
<223> OTHER INFORMATION: Xaa can be isoleusine (I), tyrosine (Y),
      histidine (H), or phenylalanine (F).
<220> FEATURE:
<221> NAME/KEY: MISC_FEATURE
<222> LOCATION: (342)..(342)
<223> OTHER INFORMATION: Xaa can be valine (V), cysteine (C),
      isoleusine (I), tryptophan (W), tyrosine (Y), or lysine (L).
<220> FEATURE:
<221> NAME/KEY: MISC_FEATURE
<222> LOCATION: (343)..(343)
<223> OTHER INFORMATION: Xaa can be asparagine (N), aspartic acid
      (D), glutamine (Q), or glutamic acid (E).

<400> SEQUENCE: 14

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
```

```
            50                  55                  60
Asn Pro His Cys Trp Ile Val Ala Asn Gly Thr Asp Lys Pro Lys Leu
 65                  70                  75                  80

Ile Phe Tyr Arg Pro Val Asp Phe Trp His Lys Val Pro Asp Glu Pro
                 85                  90                  95

Asn Glu Tyr Trp Ala Asp Tyr Phe Asp Ile Glu Leu Leu Val Lys Pro
                100                 105                 110

Asp Gln Val Glu Lys Leu Leu Pro Tyr Asp Lys Ala Arg Phe Ala Tyr
                115                 120                 125

Ile Gly Glu Tyr Leu Glu Val Ala Gln Ala Leu Gly Phe Glu Leu Met
130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
                180                 185                 190

Phe Glu Ile Gln Gln Ala Tyr Leu Leu Ala Thr Gln His Ser Glu Asn
                195                 200                 205

Asp Thr Pro Xaa Gly Asn Xaa Val Ala Leu Asn Glu Asn Cys Ala Ile
210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Phe Ala Glu Leu Val
                260                 265                 270

Ala Thr Met Lys Gln His Gln Ile Ala Leu Cys Asn Gln Leu Ala Pro
                275                 280                 285

Gly Lys Leu Tyr Gly Glu Leu His Leu Asp Cys His Gln Arg Val Ala
290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Xaa Xaa Asp Val Gly Gly Phe Met Ala Asp Glu
                340                 345                 350

Gln Gly Ala His Gln Glu Pro Pro Glu Gly His Pro Phe Leu Arg Cys
                355                 360                 365

Thr Arg Lys Ile Glu Ala Asn Gln Val Phe Thr Ile Glu Pro Gly Leu
370                 375                 380

Tyr Phe Ile Asp Ser Leu Leu Gly Asp Leu Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
                420                 425                 430

Met Thr Arg Glu Leu Glu Leu Asp
                435                 440

<210> SEQ ID NO 15
<211> LENGTH: 440
<212> TYPE: PRT
<213> ORGANISM: Artificial Sequence
```

-continued

```
<220> FEATURE:
<223> OTHER INFORMATION: Synthetic Polypeptide - Organophosphate acid
      anhydrolase
<220> FEATURE:
<221> NAME/KEY: MISC_FEATURE
<222> LOCATION: (343)..(343)
<223> OTHER INFORMATION: Xaa can be asparagine (N), aspartic acid (D),
      glutamine (Q), or glutamic acid (E).

<400> SEQUENCE: 15

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Phe Gly Asn Tyr Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Leu Xaa Asp Val Gly Gly Phe Met Ala Asp Glu
            340                 345                 350

Gln Gly Ala His Gln Glu Pro Pro Glu Gly His Pro Phe Leu Arg Cys
        355                 360                 365
```

```
Thr Arg Lys Ile Glu Ala Asn Gln Val Phe Thr Ile Glu Pro Gly Leu
    370             375             380

Tyr Phe Ile Asp Ser Leu Leu Gly Asp Leu Ala Ala Thr Asp Asn Asn
385             390             395             400

Gln His Ile Asn Trp Asp Lys Val Ala Glu Leu Lys Pro Phe Gly Gly
                405             410             415

Ile Arg Ile Glu Asp Asn Ile Ile Val His Glu Asp Ser Leu Glu Asn
            420             425             430

Met Thr Arg Glu Leu Glu Leu Asp
            435             440
```